United States Patent
Eberle et al.

(10) Patent No.: US 7,074,787 B2
(45) Date of Patent: Jul. 11, 2006

(54) MICROBIOCIDAL N-PHENYL-N-[4-(4-PYRIDYL-2-PYRIMIDIN-2-YL]-AMINE DERIVATIVES

(75) Inventors: Martin Eberle, Basel (CH); Hugo Ziegler, Basel (CH); Fredrik Cederbaum, Basel (CH); Peter Ackermann, Basel (CH); Anita Schnyder, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 322 days.

(21) Appl. No.: 10/451,930

(22) PCT Filed: Dec. 20, 2001

(86) PCT No.: PCT/IB01/02821

§ 371 (c)(1),
(2), (4) Date: Jun. 25, 2003

(87) PCT Pub. No.: WO02/053560

PCT Pub. Date: Jul. 11, 2002

(65) Prior Publication Data

US 2004/0063937 A1 Apr. 1, 2004

(30) Foreign Application Priority Data

Jan. 3, 2001 (GB) ................. 0100102.3

(51) Int. Cl.
C07D 401/04 (2006.01)
C07D 413/04 (2006.01)
A01N 43/54 (2006.01)

(52) U.S. Cl. .................. 514/235.8; 514/275; 544/122; 544/331

(58) Field of Classification Search .......... 544/122, 544/331; 514/235.8, 275
See application file for complete search history.

(56) References Cited

FOREIGN PATENT DOCUMENTS

| DE | 4034762 | 5/1992 |
|---|---|---|
| EP | 0388838 | 9/1990 |
| WO | 9509853 | 4/1995 |
| WO | 9818782 | 5/1998 |
| WO | 0193682 | 12/2001 |

*Primary Examiner*—Deepak Rao
(74) *Attorney, Agent, or Firm*—Rebecca A. Gegick

(57) ABSTRACT

The invention relates to novel N-phenyl-4-(4-pyridyl)-2-pyrimidineamine derivatives of the general formula (I) wherein the sum of (m+p) together is 0, 1, 2 or 3; n and q are independently of each other 0 or 1, and the sum of (m+p+q) together is 1, 2, 3 or 4; $R_1$ is hydrogen, halogen, alkoxy, haloalkyl, haloalkoxy or alkyl; $R_2$ is hydrogen, $C_1$–$C_6$-alkyl, $C_1$–$C_6$-haloalkyl or $C_1$–$C_6$-alkoxy; $R_{2A}$ is hydrogen, $C_1$–$C_6$-alkyl, $C_3$–$C_4$-alkenyl or $C_3$–$C_4$-alkynyl; each of $R_3$, $R_4$, $R_5$ and $R_6$ is, independently of the others, hydrogen, $C_1$–$C_6$-alkyl, $C_1$–$C_6$-haloalkyl, hydroxy-$C_1$–$C_6$-alkyl or $C_1$–$C_6$-alkoxy-$C_1$–$C_6$-alkyl, or the ring members $CR_3R_4$ or $CR_5R_6$ or $CR_2R_{2A}$ are independently of each other a carbonyl group (C=O) or a group C=S; X is C=O, C=S, S=O or O=S=O; Y is O, S, C=O, $CH_2$, —N($R_8$)—, —O—N($R_8$)—, —N($R_8$)—O— or NH—; $R_7$ is hydrogen, $C_1$–$C_4$-alkyl, $C_3$–$C_4$-alkenyl, $C_3$–$C_4$-alkynyl, —$CH_2OR_8$, $CH_2SR_8$, —C(O)$R_8$, —C(O)O$R_8$, SO2$R_8$, SO$R_8$ or S$R_8$; and $R_8$ is $C_1$–$C_8$-alkyl, $C_1$–$C_8$-alkoxyalkyl, $C_1$–$C_8$ haloalkyl or phenyl$C_1$–$C_2$-alkyl wherein the phenyl may be substituted by up to three groups selected from halo or $C_1$–$C_4$-alkyl; or a salt thereof. The invention also relates to the preparation of the compounds and to agrochemical compositions comprising at least one of those compounds as active ingredient as well as the preparation of the said compositions and to the use of the compounds or of the compositions in controlling or preventing the infestation of plants by phytopathogenic microorganisms, especially fungi.

14 Claims, No Drawings

MICROBIOCIDAL N-PHENYL-N-[4-(4-PYRIDYL-2-PYRIMIDIN-2-YL]-AMINE DERIVATIVES

This application is a 371 of International Application No. PCT/IB01/02821, filed Dec. 20, 2001 and which claims priority to GB 0100102.3, filed Jan. 3, 2001, the contents of which are incorporated herein by reference.

The present invention relates to novel N-phenyl-[4-(4-pyridyl)-pyrimidin-2-yl]-amine derivatives, to a method of protecting plants against attack or infestation by phytopathogenic organisms, such as nematodes or insects or especially microorganisms, preferably fungi, bacteria and viruses, or combinations of two or more of these organisms, by applying a N-phenyl-[4-(4-pyridyl)-pyrimidin-2-yl]-amine derivative as specified hereinafter to a part and/or to the site of a plant, to the use of said derivative for protecting plants against said organisms, and to compositions comprising said derivative as the active component. The invention further relates to the preparation of these novel N-phenyl-[4-(4-pyridyl)-pyrimidin-2-yl]-amine derivatives.

Certain N-phenyl-4-(4-pyridyl)-2-pyrimidineamine derivatives have been described in the art, e.g. in the PCT patent applications WO 95/09851 and WO 95/09853, as having pharmacological properties, mainly as tumor-inhibiting anti-cancer substances.

Surprisingly, it has now been found that the new N-phenyl-[4-(4-pyridyl)-pyrimidin-2-yl]-amines are effective in plant protection and related areas, showing advantageous properties in the treatment of plant diseases caused by organisms.

The novel N-phenyl-[4-(4-pyridyl)-pyrimidin-2-yl]-amine derivatives according to the invention are those of the formula I

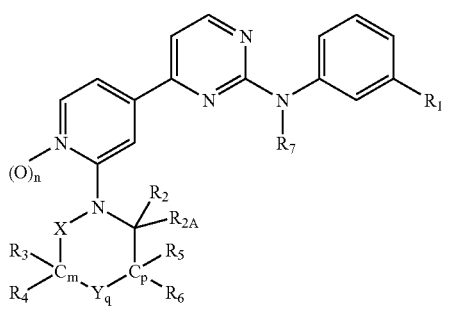

(I)

wherein
the sum of (m+p) together is 0, 1, 2 or 3;
n and q are independently of each other 0 or 1, and the sum of (m+p+q) together is 1, 2, 3 or 4;
$R_1$ is hydrogen, halogen, alkoxy, haloalkyl, haloalkoxy or alkyl;
$R_2$ is hydrogen, $C_1$–$C_6$-alkyl, $C_1$–$C_6$-haloalkyl or $C_1$–$C_6$-alkoxy;
$R_{2A}$ is hydrogen, $C_1$–$C_6$-alkyl, $C_3$–$C_4$-alkenyl or $C_3$–$C_4$-alkynyl;
each of $R_3$, $R_4$, $R_5$ and $R_6$ is, independently of the others, hydrogen, $C_1$–$C_6$-alkyl, $C_1$–$C_6$-haloalkyl, hydroxy-$C_1$–$C_6$-alkyl or $C_1$–$C_6$-alkoxy-$C_1$–$C_6$-alkyl, or the ring members $CR_3R_4$ or $CR_5R_6$ or $CR_2R_2A$ are independently of each other a carbonyl group (C=O) or a group C=S;
X is C=O, C=S, S=O or O=S=O;
Y is O, S, C=O, $CH_2$, —N($R_8$)—, —O—N($R_8$)—, —N($R_8$)—O— or —NH—;
$R_7$ is hydrogen, $C_1$–$C_4$-alkyl, $C_3$–$C_4$-alkenyl, $C_3$–$C_4$-alkynyl, —$CH_2OR_8$, $CH_2SR_8$, —C(O)$R_8$, —C(O)O$R_8$, $SO_2R_8$, $SOR_8$ or $SR_8$; and
$R_8$ is $C_1$–$C_8$-alkyl, $C_1$–$C_8$-alkoxyalkyl, $C_1$–$C_8$ haloalkyl or phenyl$C_1$–$C_2$-alkyl wherein the phenyl may be substituted by up to three groups selected from halo or $C_1$–$C_4$-alkyl; or a salt thereof.

The general symbols and expressions used above preferably are defined as below:

Halogen is fluorine, bromine, iodine or preferably chlorine.

Haloalkyl is preferably $C_1$–$C_6$-alkyl, more preferably lower alkyl, that is linear or branched and is substituted by one or more, for example in the case of halo-ethyl up to five, halogen atoms, especially fluorine. An example is trifluoromethyl.

Haloalkoxy is preferably $C_1$–$C_6$-alkoxy, more preferably lower alkoxy, that is linear or branched and that is substituted by one or more, for example in the case of halo-ethyl up to five, halogen atoms, especially fluorine; trifluoromethoxy and 1,1,2,2-tetrafluoroethoxy are especially preferred.

Alkyl—as a group per se and as a structural element of hydroxyalkyl, alkoxy, alkenyl, alkynyl or haloalkoxy—is preferably $C_1$–$C_6$-alkyl, more preferably lower alkyl, and is linear i.e. methyl, ethyl, propyl, butyl, pentyl or hexyl, or branched, e.g. isopropyl, isobutyl, sec.-butyl, tert.-butyl, isopentyl, neopentyl or isohexyl. Lower alkyl is preferably methyl or ethyl. Specific examples of alkenyl and alkynyl include allyl, 2-butenyl, 3-butenyl, propargyl, 2-butinyl and 3 butynyl.

Preferred among the compounds to be used according to the invention is a compound wherein within the N-linked heterocycle attached to the 2-position of the pyridine ring, namely the moiety

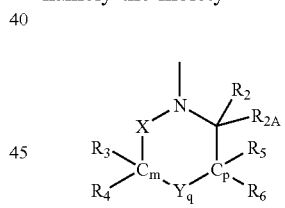

is one in which the sum of the index numbers m+p+q is 2, 3 or 4, thus indicating various 5- to 7-membered ring systems, which are conceivable under the given definitions and which are common in the art of heterocycles. More preferably, this moiety represents a 5- and 6-membered ring system (m+p+q is 2 or 3), preferably a 5-membered ring system. Thus examples of the moieties include N-oxazolidin-2-one, N-oxazolidin-2-thione, N-[1,2,3]oxathiazolidine-2-oxide, N-[1,2,3]oxathiazolidine-2,2-dioxide, N-pyrrolidin-2-one, N-pyrrolidin-2-thione, N-pyrrolidine-2,5-dione, N-thiazolidin-2-one, N-4-methylene-oxazolidin-2-one, N-piperidine-2,6-dione, N-morpholine-2,3-dione, N-morpholine-2,5-dione, N-imidazolidin-2-one, N-[[1,2,4]-oxazolidin-5-one, N-1,2,4]-oxazolidin-3-one, N-[1,2,5]oxadiazinan-6-one, N-[1,2,4]oxadiazinan-3-one, azepan-2-one or [1,3]oxazinan-2-one.

More preferred ring systems for the moiety positioned at the 2-position of the pyridyl ring are those selected from the group comprising N-oxazolidin-2-one, N-oxazolidin-2-thione, N-[1,2,3]oxathiazolidine-2-oxide and N-pyrrolidin-2-one.

The compounds of formula I can form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid, oxalic acid or amino acids, such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid.

The pyridine-N-oxides of formula I can form acid addition salts with strong acids, such as hydrochloric acid, nitric acid, phosphoric acid or sulfonic acids, such as benzene-sulfonic acid.

Formula I according to the invention shall include all the possible isomeric forms, as well as mixtures, e.g. racemic mixtures, and any mixtures of rotamers.

In view of the close relationship between the compounds of formula I in free form and in the form of their salts, including also salts that can be used as intermediates, for example in the purification of the compounds of formula I or in order to identify those compounds, herein-before and hereinafter any reference to the (free) compounds is to be understood as including also the corresponding salts, where appropriate and expedient.

Among the compounds of formula I according to the present invention the following groups of compounds are preferred. These groups are those wherein $R_1$ is chlorine, fluorine, trifluoromethyl, trifluoromethoxy, or 1,1,2,2-tetrafluoroethoxy, or $R_1$ is chlorine, or $R_2$ is hydrogen, methyl, trifluoromethyl or ethyl, or $R_2$ is methyl or trifluoromethyl, or $R_2$ is methyl, or $R_{2A}$ is hydrogen or methyl; or $R_{2A}$ is hydrogen; or $R_3$, $R_4$, $R_5$ and $R_8$ independently of each other are hydrogen, methyl, hydroxymethyl, hydroxyethyl, or methoxyethyl, or one of $R_3$ and $R_4$ or one of $R_5$ and $R_6$ is hydrogen or methyl, while the other one is hydrogen, methyl, hydroxymethyl, hydroxyethyl, or methoxyethyl, or $R_3$ and $R_4$ are hydrogen, or $R_5$ and $R_6$ independently of each other are hydrogen or methyl, or $R_7$ is hydrogen, methyl, ethyl, allyl, propargyl, methoxymethyl, thiomethoxymethyl or ethoxymethyl, or $R_7$ is hydrogen or methoxymethyl, or X is carbonyl, C=S, or S=O; or X is carbonyl, or Y is oxygen, sulfur, —O—N(CH$_3$)—, or —N(CH$_3$)—O—, or Y is oxygen, or X is carbonyl, C=S, or S=O and Y is oxygen.

n is zero, or m is zero and p and q are each one.

Further preferred subgroups comprise those compounds of formula I wherein a) $R_1$ is chlorine, fluorine, trifluoromethyl, trifluoromethoxy, or 1,1,2,2-tetrafluoroethoxy; $R_2$ is hydrogen, methyl, trifluoromethyl or ethyl; $R_{2A}$ is hydrogen or methyl; $R_5$ and $R_6$ independently of each other are hydrogen, methyl, hydroxymethyl, hydroxyethyl, or methoxyethyl; $R_7$ is hydrogen, methyl, ethyl, allyl, propargyl, or methoxymethyl; X is carbonyl, C=S, or S=O; Y is oxygen, sulfur, —O—N(CH$_3$)—, or —N(CH$_3$)—O—; m and n are zero and p and q are each one; or b) $R_1$ is chlorine; $R_2$ is methyl or trifluoromethyl; $R_{2A}$ is hydrogen or methyl; one of $R_5$ and $R_6$ is hydrogen or methyl, while the other one is hydrogen, methyl, hydroxymethyl, hydroxyethyl, or methoxyethyl; $R_7$ is hydrogen or methoxymethyl; X is carbonyl; Y is oxygen; m and n are zero and p and q are each one; or c) $R_1$ is chlorine; $R_2$ is methyl; $R_{2A}$ is hydrogen; $R_5$ and $R_6$ independently of each other are hydrogen or methyl; $R_7$ is hydrogen or methoxymethyl; X is carbonyl; Y is oxygen; m and n are zero and p and q are each one.

Preferred individual compounds of the formula I are:

3-{4-[2-(3-chloro-phenylamino)-pyrimidin-4-yl]-pyridin-2-yl}-oxazolidin-2-one,

N-{4-[2-(3-chloro-phenylamino)-pyrimidin-4-yl]-pyridin-2-yl}-pyrrolidin-2-one, (3-chloro-phenyl)-{4-[2-(2-oxo-[1,2,3]oxathiazolidin-3-yl)-pyridin-4-yl]-pyrimidin-2-yl}-amine, 3-{4-[2-(3-fluoro-phenylamino)-pyrimidin-4-yl]-pyrimidin-2-yl}-4-methyl-oxazolidin-2-one, 3-{4-[2-(3-trifluoromethyl-phenylamino)-pyridin-4-yl]-pyridin-2-yl}-4-methyl-oxazolidin-2-one, (3-chloro-phenyl)-{4-[2-(4-methyl-2-oxo-[1,2,3]oxathiazolidin-3-yl)-pyridin-4-yl]-pyrimidin-2-yl}-amine, 1-{4-[2-(3-chloro-phenylamino)-pyrimidin-4-yl]-pyridin-2-yl}-5-methyl-pyrrolidin-2-one, 3-{4-[2-(3-chloro-phenylamino)-pyrimidin-4-yl]-pyridin-2-yl}-4-ethyl-oxazolidin-2-one, 3-{4-[2-(3-chloro-phenylamino)-pyrimidin-4-yl]-pyridin-2-yl}-4-n-propyl-oxazolidin-2-one, 3-{4-[2-(3-chloro-phenylamino)-pyrimidin-4-yl]-pyridin-2-yl}-4-i-propyl-oxazolidin-2-one, 3-{4-[2-(3-chloro-phenylamino)-pyrimidin-4-yl]-pyridin-2-yl}-5-methyl-oxazolidin-2-one, 3-{4-[2-(3-chloro-phenylamino)-pyrimidin-4-yl]-pyridin-2-yl}-4-methyl-oxazolidin-2-one, 3-{4-[2-(3-chloro-phenylamino)-pyrimidin-4-yl]-pyridin-2-yl}-4-methyl-oxazolidine-2-thione, (S)-3-{4-[2-(3-Chloro-phenylamino)-pyrimidin-4-yl]-pyridin-2-yl}-4-methyl-oxazolidin-2-one, 3-{4-[2-(3-Chloro-phenylamino)-pyrimidin-4-yl]-pyridin-2-yl}-4-trifluoromethyl-oxazolidin-2-one, (R)-3-{4-[2-(3-Chloro-phenylamino)-pyrimidin-4-yl]-pyridin-2-yl}-4-methyl-oxazolidin-2-one, 3-{4-[2-(3-Chloro-phenylamino)-pyrimidin-4-yl]-pyridin-2-yl}-4-trifluoromethyl-[1,3]oxazinan-2-one 3-{4-[2-(3-Chloro-phenylamino)-pyrimidin-4-yl]-pyridin-2-yl}-4-methyl-[1,3]oxazinan-2-one, 1-{4-[2-(3-chloro-phenylamino)-pyrimidin-4-yl]-pyridin-2-yl}-5-trifluoromethyl-pyrrolidin-2-one, 3-(4-{2-[(3-chloro-phenyl)-methoxymethyl-amino]-pyrimidin-4-yl}-pyridin-2-yl)-4-methyl-oxazolidin-2-one.

The compounds according to the invention may be prepared according to methods per se known in the art (this does mean, however, that, where novel compounds are produced, the respective process of manufacture is also novel). The procedures for the preparation of compounds of formula I may be outlined as follows:

A) reacting a compound of the formula (II)

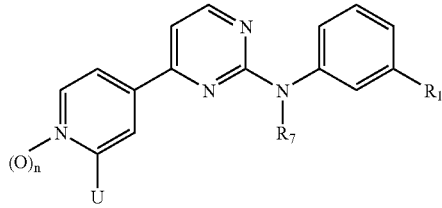

(or a salt thereof) wherein U is a leaving group, especially halogen, for example fluoro, chloro, bromo or iodo, and the other moieties have the meanings given for a compound of the formula I, with a cyclic amine ring system of the formula III

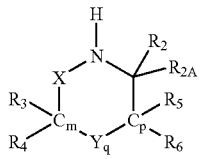

(or a salt thereof) wherein $R_2$ to $R_6$, $R_{2A}$, X, Y, m, p and q have the meanings given for a compound of the formula I, in the presence of a base and a metal catalyst, such as palladium(II) or palladium(O) complexes, or in the presence of a base, such as sodium hydride, potassium carbonate, potassium tert-butoxide or B) cyclize a compound of the formula IV

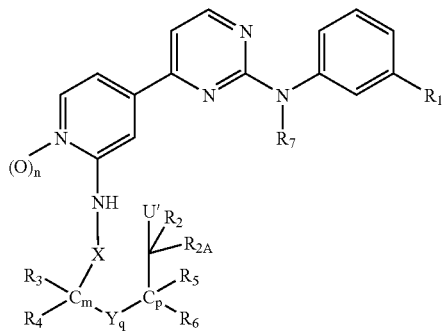

wherein $R_1$ to $R_7$, $R_{2A}$, X, Y, n, m, p and q have the meanings given for a compound of the formula I and U' is a leaving group, especially halo, for example chloro, bromo or iodo, or sulfonyloxy, for example mesyloxy, trifluoromethansulfonyloxy, tosyloxy or benzenesulfonyloxy by heating it optionally in the presence of a base such as pyridine, triethylamine, sodium carbonate, etc., or C) reacting a compound of the formula V

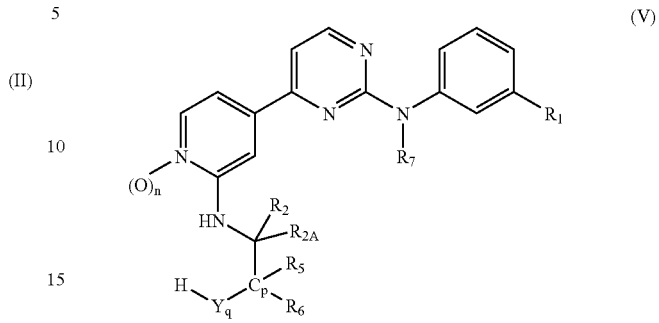

wherein q is 1 and $R_1$, $R_2$, $R_{2A}$, $R_5$, $R_6$, $R_7$, Y, n and p have the meanings given for a compound of the formula I, with phosgene, di- or triphosgene, carbonyldiimidazol, thiophosgene, thiocarbonyldiimidazol or thionylchloride thus obtaining a compound of the subformula Ia

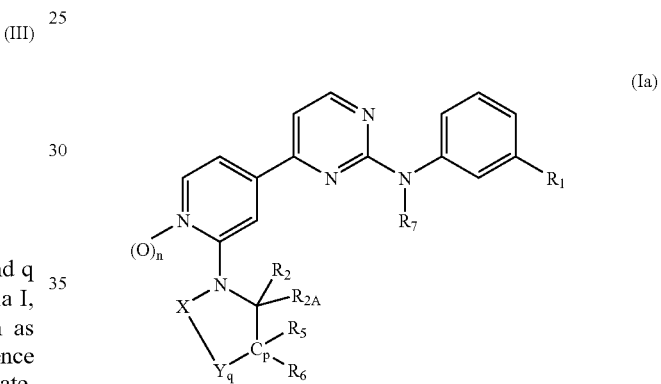

wherein X is C=O, C=S or S=O, q is 1 and $R_1$, $R_2$, $R_{2A}$, $R_5$, $R_6$, $R_7$, Y, n and p have the meanings given for a compound of the formula I, or D) by oxidizing of a compound of the subformula Ib

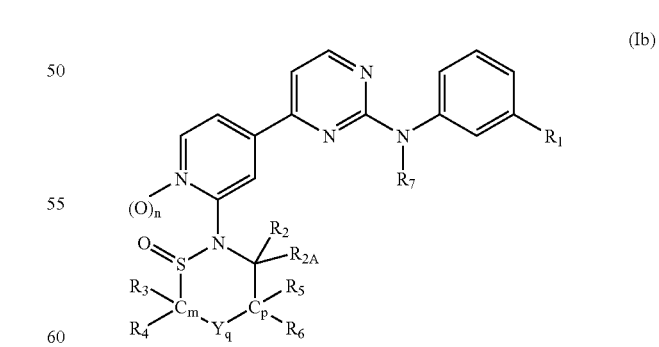

wherein $R_1$ to $R_7$, $R_{2A}$, Y, n, m, p and q have the meanings given for a compound of the formula I using an oxidizing amount of an oxidizing agent, for example $NaIO_4/RuCl_3$, $NaOCl/RuO_3$ or $KMnO_4$, in order to form a compound of the formula I, wherein X is O=S=O, or E) reacting a compound of the formula VI

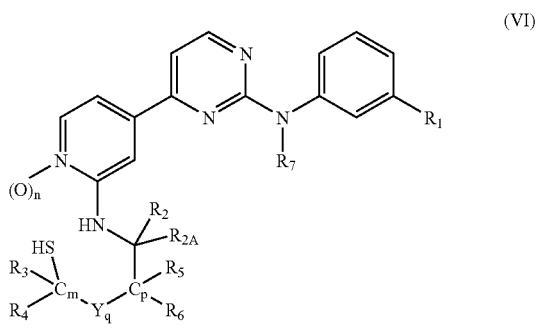

wherein $R_1$ to $R_7$, $R_{2A}$, Y, n, m, p and q have the meanings given for a compound of the formula I with an oxidizing amount of an oxidizing agent, for example iodine, in order to form a compound of the formula I, wherein X is S=O.

The reaction types A to E and additional methods which can be applied per se or as analogous procedures for the synthesis of compounds of the formula I are described for example in Organic Letters 2(8), 1101–1104 (2000); Organic Letters 3 (16), 2539–2541 (2001); Organic Letters 2(5), 625–627 (2000); Tetrahedron Letters 40(11), 2035–2038 (1999); Heterocycles 48(3), 481–489 (1998); Journal of Organic Chemistry 55(13), 4156–4162 (1990); Journal of Organic Chemistry 58(3), 696–699 (1993); Journal of Organic Chemistry 50(1), 1–4 (1985); Patent Application GB 2267287 A (1993); Patent Application EP-A-497695 (1992); Organic Magnetic Resonance 12(8), 481–489 (1979); Journal of the Chemical Society, Perkin Trans.2, 1207–1210 (1978); Patent Application JP 54024869 (1979); Yakugaku Zasshi 98(6), 817–821 (1978); Heterocycles 7(2), 919–925 (1977); Chemical Abstracts 77:139931; Zhurnal Organicheskoi Khimii 6(6), 1305–1308 (1970). The palladium catalysts suitable for the C—N linkage reaction (Buchwald-Hartwig amination) of the compound of the formula II with the cyclic amine ring system of the formula III are generally palladium(II) or palladium(0) complexes. They can be prepared in a separate step such as, for example, dichloro[1,1'-bis(diphenylphosphino)ferrocene]palladium or $PdCl_2(BINAP)$. The palladium catalyst can also be prepared "in situ" from palladium(II) or palladium(0) compounds, such as, palladium(II) dichloride, palladium(II) acetate, bis(dibenzylideneacetone)palladium(0), tris(dibenzylideneacetone) dipalladium, and corresponding ligands.

Examples of suitable ligands include but are in no way limited to tris(tert-butyl)phosphine, tricyclohexylphosphine ($PCy_3$), 2,2'-(diphenylphosphino)-bisnaphthalene (BINAP), 1,1'-bis(diphenylphosphino)ferrocene (dppf), 1,1'-bis(di-tert-butylphosphino)ferrocene, 1,2-bis(diphenylphosphino)ethane, 1,3-bis(diphenylphosphino)propane, 1,4-bis(diphenylphosphino)butane, bis(2-(diphenylphosphino)phenyl) ether (DPE-phos), 4,5-bis (diphenylphosphino)-9,9-dimethylxanthanene (Xantphos), 2-(di-tert-butylphosphino) biphenyl, 2-(dicyclohexylphosphino)biphenyl, 2-dicyclohexylphosphino-2'-(N,N'-dimethylamino)biphenyl, 2-di-tert-butylphosphino-2'-(N,N'-dimethylamino)biphenyl.

Exemplary bases include such as, for example, sodium tert-butoxide, potassium tert-butoxide, sodium amide, lithium diusopropyl amide (LDA), lithium bis(trimethylsilyl)amide, sodium bis(trimethylsilyl)amide, sodium methylate, sodium phenolate, $Cs_2CO_3$, $K_3PO_4$.

The compounds of the formula II, V and VI may be prepared in accordance with manufacturing processes described in WO 95/09853, or in analogy to the methods described therein.

The compounds of the formula III are known or may be prepared in analogy to the synthesis methods described in Organic Letters 2(5), 625–627 (2000); Patent Application EP-A-350002 (1990) or in the above mentioned literature.

The compounds of the formula IV are novel und may be prepared by reacting a compound of the formula VII

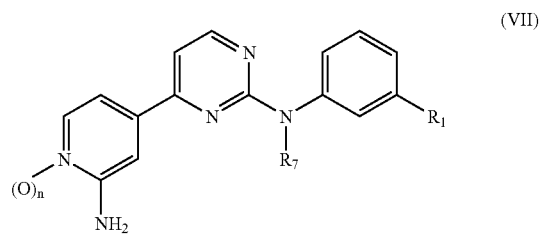

wherein $R_1$, $R_7$ and n have the meanings given for a compound of the formula I, with a compound of the formula VIII

wherein $R_2$ to $R_6$, $R_{2A}$, U', X, Y, m, p and q have the meanings given for a compound of the formula IV and U" is a leaving group, especially chloro, or is oxygen which forms an anhydride.

The preparation of a compound of the formula VII is described in the PCT application WO 95/09851.

A compound of the formula II, wherein $R_7$ is hydrogen, may be obtained preferably by reacting a compound of the formula IX

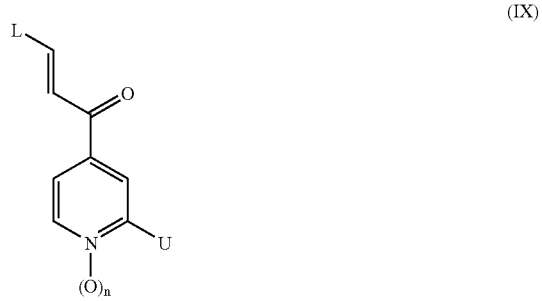

(or—if n is 0—a salt thereof) wherein L is a leaving group, especially alkoxy, such as lower alkoxy, esterified OH (especially tosyloxy), or di-(lower alkylamino), U is a leaving group (preferably halo, such as chloro, bromo or iodo) and n is 0 or 1, with a guanidino compound of the formula X,

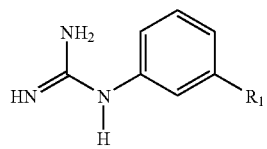

(or a salt thereof) wherein $R_1$ is as defined for a compound of the formula I. The reaction preferably in conducted under conditions analogous to those mentioned in PCT application WO 95/09583, that is, in a suitable solvent or suspending agent, for example a suitable alcohol, such as isopropanpol, or 2-butanol, at a temperature from room temperature (approximately +20° C.) to +150° C., e.g. under reflux.

A compound of the formula II, wherein $R_7$ is —$CH_2OR_8$, —$C(O)R_8$ or —$C(O)OR_8$, may preferably be obtained by reacting a compound of the formula II, wherein $R_7$ is hydrogen, with one of the following reagents: Hal-$CH_2OR_8$, Hal-$C(O)R_8$, Hal-$C(O)OR_8$ rasp. $O(C(O)R_8)_2$, wherein Hal means halogen like chlorine, bromine or iodine.

The compound of the formula IX are known or may be obtained in accordance with methods that are known in the art, e.g. by reacting a compound of the formula XI

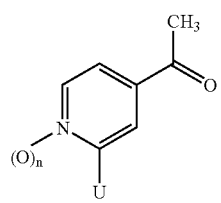

wherein n is 0 or 1 and wherein U is a leaving group, preferably as defined for a compound of the formula (IX), either (i) under Claisen or analogue condensation reaction conditions (leading to a free hydroxy instead of the leaving group L in a compound of the formula IX; this free hydroxy group can then be converted into a leaving group, for example by ether formation with an alkylalkohol ("Alkoxy-H";), yielding alkoxy as L, such as lower alkoxy, or by reaction with an acid or an active ester derivative, e.g. an acid chloride, yielding esterified OH (especially tosyloxy); or to alkoxy L, depending on the reaction conditions), or (ii) preferably by reaction with an N,N-di-(lower alkyl)-formamide di-lower alkylacetal, especially N,N-di-(methyl)formamide di-methylacetal, analogous to the procedure described in European Patent Application EP-A-0233461, which is incorporated by reference, e.g. by reaction in the respective N,N-di-(lower alkyl)-formamide di-lower alkylacetal at a temperature between room temperature and the boiling point of the reaction mixture, especially under reflux conditions.

An intermediate of the formula (XI) may, for example, be obtained by reaction of a metallated methyl derivative of the formula (XII)

$CH_3$-Metal (XII)

wherein Metal stands preferably for Mg-Hal (Hal=halogen) or Li, with a 4-pyridyl-carbonic acid derivative of the formula (XIII)

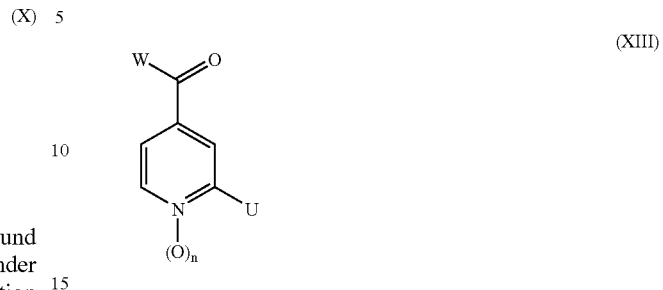

wherein U and n have the meanings given for a compound of the formula IX, and W is a leaving group, preferably N-lower alkyl-N-lower alkoxy-amino or halogen, under standard conditions for alkylation reactions.

Alternatively, an intermediate of the formula XI, wherein n is 0, may be obtained by reaction of a metallated pyridine derivative of the formula XIV

wherein U is a leaving group, preferably as defined for a compound of the formula IX, and Metal stands for Mg-Hal (Hal=halogen) or Li, under standard conditions for alkylation reactions with an acetyl equivalent of the formula XV

wherein Z is halo, or forms with the rest of the molecule an amide, an alkoxyamide, an anhydride or the like; or Z is hydrogen (meaning that the compound XV is acetaldehyde), resulting after the reaction in an alcohol that is then oxidized with a selective oxidant, for example in the presence of oxalylchloride and dimethyl sulfoxide, to the ketone intermediate of the formula XI.

A starting material of the formula X may be prepared (preferably obtaining an acid addition salt) by reaction of an aniline derivative of the formula XVI

wherein $R_1$ is as defined for a compound of formula I, with cyanamide (NC-$NH_2$) in a suitable solvent, e.g. an alcohol, such as a lower alkanol, for example (i) in the presence of equimolar amounts of the salt-forming acid, for example nitric acid, or (ii) in the presence of a clear, for example 60%, excess of a mineral acid, such as hydrochloric acid, where an ammonium salt of the desired salt-forming acid is added when the reaction is complete; at a temperature between room temperature and +150° C., e.g. under reflux.

Compounds of the formulae XIII, XIV and XVI may be prepared according to methods that are known in the art.

The synthesis of many of the starting materials and intermediates may also be done as described in or in analogy to the processes described in WO 95/09853.

In all intermediates, functional groups that shall not participate in the intended reactions may be protected and deprotected at appropriate stages in order to avoid side reactions—appropriate protecting groups and methods for their introduction and removal can be found e.g. in WO 95/09853.

The present invention also relates to novel starting materials and/or intermediates and to processes for the preparation thereof. The starting materials used and the reaction conditions chosen are preferably such that the compounds shown in this disclosure as being especially preferred or to be used preferably are obtained. Especially preferred among the process conditions are those described in the examples below, or analogous procedures.

The invention also relates to compositions which comprise the compounds of the formula I, or a salt thereof, as an active component, in particular plant-protecting compositions, and also to their use in the agricultural sector or related areas.

Active compounds of the formula I are customarily used in the form of compositions and may be added, simultaneously or successively, to the surface or plant to be treated together with additional active compounds. These additional active compounds may be either fertilizers, trace element-supplying agents or other preparations which influence plant growth. It is also possible, in this context, to use selective herbicides, such as insecticides, fungicides, bactericides, nematicides or molluscicides, or mixtures of several of these preparations, additionally, where appropriate, together with excipients, surfactants or other administration-promoting additives which are customary in formulation technology (designated collectively as carrier materials herein).

Suitable excipients and additives may be solid or liquid and are those substances which are appropriate in formulation techology, for example natural or regenerated minerals, solvents, dispersants, wefting agents, adhesives, thickening agents, binding agents or fertilizers.

A preferred method for applying a compound of formula I, or an agrochemical composition which comprises at least one of these compounds, is administration to the leaves (foliar application). The frequency and rate of administration depend upon the risk of infestation by the corresponding pathogen. The compounds of formula I can, however, also penetrate the plant through the roots via the soil (systemic action). If the locus of the plant is impregnated with a liquid formulation or if the substances are introduced in solid form into the soil, e.g. in the form of granules (soil application). In paddy rice crops, such granules can be applied in metered amounts to the flooded rice fields. In order to treat seeds, the compounds of formula I can, however, also be applied to the seeds (coating), either by impregnating the grains or tubers with a liquid formulation of the active ingredient, or by coating them with a solid formulation.

Advantageous rates of application are in normally from 5 g to 2 kg of active ingredient (a.i.) per hectare (ha), preferably from 10 g to 1 kg of a.i./ha, especially from 20 g to 600 g a.i./ha. When the compound are used as seed dressings, dosages of from 10 mg to 1 g of active ingredient per kg seed are advantageous employed. The agrochemical compositions generally comprise 0.1 to 99% by weight, preferably 0.1 to 95% by weight, of a compound of formula I, 99.9 to 1% by weight, preferably 99.8 to 5% by weight, of a solid or liquid adjuvant and 0 to 25% by weight, preferably 0.1 to 25% by weight, of a surfactant. Whereas commercial products will preferably be formulated as concentrates, the end user will normally employ dilute formulations.

The compositions may also comprise further auxiliaries, such as fertilizers and other active ingredients for obtaining special desirable biological effects.

The compounds of formula I may be used preventatively and/or curatively in the sector of agronomics and related technical areas as active ingredients for controlling plant pests. The active ingredients of formula I according to the invention are notable for their good activity even at low concentrations, for their good plant tolerance and for their environmentally friendly nature. They have very advantageous, especially systemic, properties and may be used to protect a plurality of cultivated plants. Using the active ingredients of formula I on plants or plant parts (fruit, flowers, leaves, stems, tubers, roots) of various crops, the pests appearing can be controlled or destroyed, whereby the parts of plants which grow later also remain protected, e.g. from phytopathogenic microorganisms.

The compounds I may additionally be used as a dressing to treat seeds (fruits, tubers, corms) and plant cuttings to protect against fungal infections and against phytopathogenic fungi occurring in the soil.

The compounds I are effective for example against the following classes of related phytopathogenic fungi: *Fungi imperfecti* (e.g. *Botrytis, Pyricularia, Helminthosporium, Fusarium, Septoria, Cercospora* and *Alternaria*); *Basidiomycetes* (e.g. *Rhizoctonia, Hemileia, Puccinia*); *Ascomycetes* (e.g. *Venturia* and *Erysiphe, Podosphaera, Monilinia, Uncinula*) and *Oomycetes* (e.g. *Phytophthora, Pythium, Plasmopara*).

Target crops for the plant-protecting usage in terms of the invention are for example the following plant cultivars: cereals (wheat, barley, rye, oats, rice, maize, sorghum and related species); beet (sugar beet and fodder beet); pome, stone and berry fruit (apples, pears, plums, peaches, almonds, cherries, strawberries, raspberries and blackberries); legumes (beans, lentils, peas, soya); oil crops (rape, mustard, poppy, olives, sunflowers, coconut, castor oil, cocoa, peanut); cucumber plants (squashes, cucumber, melons); citrus fruits (oranges, lemons, grapefruits, mandarines); vegetables (spinach, lettuce, asparagus, cabbage varieties, carrots, onions, tomatoes, potatoes, paprika); laurels (avocado, cinnamonium, camphor) and plants such as tobacco, nuts, coffee, aubergines, sugar cane, tea, pepper, vines, hops, bananas and natural rubber plants, as well as ornamental plants.

Further areas of application for the active ingredients according to the invention are the protection of stores and material, where the storage matter is protected against putrescence and mould.

The compounds I are used in unchanged form or preferably together with customary excipients in formulation techniques. To this end, they are conveniently processed in known manner e.g. into emulsion concentrates, coatable pastes, directly sprayable or diluable solutions, diluted emulsions, wettable powders, soluble powders, dusts or granules, e.g. by encapsulation into for example polymeric materials. As with the type of medium, the application processes, such as spraying, atomizing, dusting, scattering, coating or pouring are similarly chosen according to the desired aims and the prevailing conditions.

Suitable substrates and additives may be solid or liquid and are useful substances in formulation techniques, e.g. natural or regenerated mineral substances, dissolving aids, dispersants, wetting agents, tackifiers, thickeners or binding agents.

The compounds of formula I may be mixed with further active ingredients, e.g. fertilizers, ingredients providing trace elements or other active ingredients used in the plant protection science, especially further fungicides. In doing so, in some cases synergistic enhancement of the biological effects may occur.

Preferred active ingredients advantageous as additives to the compositions comprising the active ingredient of formula I are:

Azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostro-bin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

One preferred method of application of an active ingredient of formula I or of an agrochemical composition containing at least one of these active ingredients is foliar application. The frequency and amount of application depend on the severity of the attack by the pathogen in question. However, the active ingredients I may also reach the plants through the root system via the soil (systemic action) by drenching the locus of the plant with a liquid preparation or by incorporating the substances into the soil in solid form, e.g. in the form of granules (soil application). In rice cultivations, these granules may be dispensed over the flooded paddy field. The compounds I may however also be applied to seed grain to treat seed material (coating), whereby the grains or tubers are either drenched in a liquid preparation of the active ingredient or coated with a solid preparation.

The compositions are produced in known manner, e.g. by intimately mixing and/or grinding the active ingredient with extenders such as solvents, solid carriers and optionally surfactants.

Favourable application rates are in general 1 g to 2 kg of active substance (AS) per hectare (ha), preferably 10 g to 1 kg AS/ha, especially 20 g to 600 g AS/ha. For usage as a seed dressing, it is advantageous to use dosages of 10 mg to 1 g active substance per kg of seed grain.

While concentrated compositions are preferred for commercial usage, the end user normally uses diluted compositions.

Formulations may be prepared analogously to those described for example in WO 97/33890.

EXAMPLES

The subsequent examples are intended to illustrate the invention, without however limiting the scope thereof.

Synthesis Example 1

3-{4-[2-(3-Chloro-phenylamino)-pyrimidin-4-yl]-pyridin-2-yl}-oxazolidin-2-one

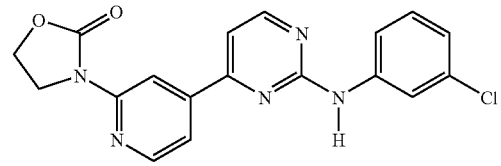

Phosgene in toluene (1.9 ml of a 20% commercial solution, 3.5 mmol) is added within five minutes to a solution of 2-{4-[2-(3-chloro-phenylamino)-pyrimidin-4-yl]-pyridin-2-ylamino}-ethanol (0.88 g, 2.6 mmol) and triethylamine (1.7 ml, 11.7 mmol) in absolute THF (20 ml) at 50° C. After stirring the resulting suspension for one hour at room temperature it is partitioned between ethyl acetate and water. The organic phase is separated, dried over magnesium sulfate, filtered and evaporated under reduced presssure. The residue is purified by silicagel chromatography to give the title compound, m.p. 162–163° C.

Synthesis Example 2

3-{4-[2-(3-Chloro-phenylamino)-pyrimidin-4-yl-pyridin-2-yl}-oxazolidine-2-thione

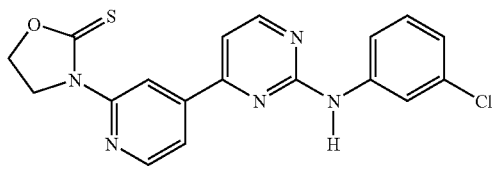

A mixture of 2-{4-[2-(3-chloro-phenylamino)-pyrimidin-4-yl]-pyridin-2-ylamino}-ethanol (0.67 g, 2.0 mmol) and thiocarbonyldiimidazole (0.38 g, 2.1 mmol) in absolute THF (20 ml) is stirred at room temperature for one hour. The reaction mixture is partitioned between ethyl acetate and water. The organic phase is separated, dried over magnesium sulfate, filtered and evaporated under reduced presssure. The residue is purified by silicagel chromatography to give the title compound, m.p. 213–214° C.

Synthesis Example 3

(3-Chloro-phenyl)-{4-[2-(2-oxo-[1,2,3]oxathiazolidin-3-yl)-pyridin-4-yl]-pyrimidin-2-yl}-amine

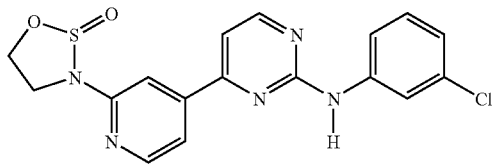

A solution of sulfonyl chloride (0.63 g, 5.3 mmol) in THF (2 ml) is added within 5 minutes to a solution of 2-{4-(2-(3-chloro-phenylamino)-pyrimidin-4-yl]-pyridin-2-ylamino}-ethanol (1.50 g, 4.4 mmol) and triethylamine (3.0 ml, 22 mmol) in absolute THF (20 ml) at +5° C. After stirring the resulting suspension for four hours at room temperature it is partitioned between ethyl acetate and water. The organic phase is separated, dried over magnesium sulfate, filtered and evaporated under reduced presssure. The residue is purified by silicagel chromatography to give the title compound, m.p. 202–203° C.

Synthesis Example 4

1-{4-[2-(3-Chloro-phenylamino)-pyrimidin-4-yl]-pyridin-2-yl}-pyrrolidin-2-one

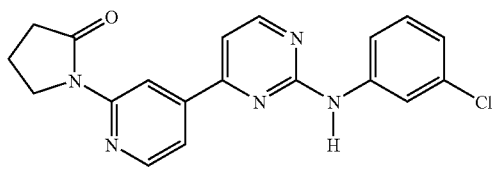

To a solution of (3-chloro-phenyl)-[4-(2-chloro-pyridin-4-yl)-pyrimidin-2-yl]-amine (4.8 g, 0.015 mol) in pyrrolidon (20 ml) is added sodium hydride (1.93 g, 0.06 mmol of a 75% dispersion in oil) in several portions. The reaction temperature is slowly raised to +150° C. After 30 minutes the heating bath is removed and the mixture is poured onto crushed ice. The reaction mixture is partitioned between ethyl acetate and water. The organic phase is separated, dried over magnesium sulfate, filtered and evaporated under reduced presssure. The residue is purified by silicagel chromatography and recrystallized from ethyl acetate to give the title compound, m.p. 165–166° C.

Synthesis Example 5

3-(4-{2-[(3-Chloro-phenyl)-methoxymethyl-amino]-pyrimidin-4-yl}-pyridin-2-yl)-4-methyl-oxazolidin-2-one

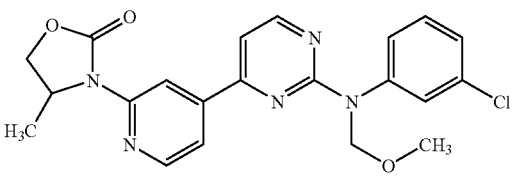

Potassium t-butoxide (0.235 g, 2.1 mmol) is added at room temperature to a solution of 3-{4-[2-(3-chloro-phenylamino)-pyrimidin-2-yl}-4-methyl-oxazolidin-2-one (0.5 g, 1.3 mmol). After stirring the mixture for 10 minutes chloromethylmethylether (0.17 g, 2.1 mmol) in THF (3 ml) is added. The mixture is stirred for additional 5 hours at this temperature. Dilution with ethyl acetate, washing with brine, drying over magnesium sulfate, filtering and evaporation of the solvent gives the title compound in form of a slightly colored oil; $^1$H-NMR (DMSO): 8.70 (s, 1H); 8.51 (d, 1H); 8.48 (d, 1H); 7.68 (d, 1H); 7.47–7.23 (m, 5H); 5.39 (s,2H); 4.87–4.74 (m,1H); 4.50 (dd, 1H); 4.08 (dd,1H); 3.25 (s,3H); 1.33 (d,3H).

Synthesis Example 6

1-{4-[2-(3-Chloro-phenylamino)-pyrimidin-4-yl]-pyridin-2-yl}-5-methyl-pyrrolidin-2-one

In a Schlenk tube (3-chloro-phenyl)-[4-(2-chloro-pyridin-4-yl)-pyrimidin-2-yl]-amine (0.95 g), NaOtBu (0.29 g), dppf (0.1 g), Pd(OAc)$_2$ (0.01 g) and 4-methylpyrrolidin-2one (0.2 g) are added: Three consecutive cycles of vacuum/argon are applied. Thereafter, 10 ml of degassed dioxane is added and the solution is heated to 120° C. (external temperature) for 8 hours. The solvent is removed under vacuum and the crude product is purified over column chromatography (eluent; EE/MeOH=9/1) yielding the title compound, m.p. 162–164° C.

Synthesis Example 7

3-{4-[2-(3-Chloro-phenylamino)-pyrimidin-4-yl]-pyridin-2-yl}-4-methyl-oxazolidin-2-one

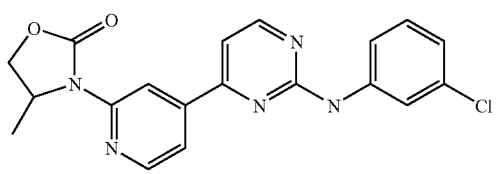

A solution of Xantphos (0.018 g) and Pd$_2$(dba)$_3$ (0.014 g) in toluene (2 ml) is stirred under argon at room temperature for 20 minutes. Then (3-chloro-phenyl)-[4-(2-chloro-pyridin-4-yl)-pyrimidin-2-yl]-amine (0.20 g), (R)-4-methyl-oxazolidin-2-one (0.127 g), NaOtBu (0.085 g) and toluene ((2 ml) are added. The reaction mixture is refluxed at 120° C. for 1 hour. After this time the mixture is cooled to room temperature, diluted with ethyl acetate, and washed with water. The organic layer is dried over Na$_2$SO$_4$ and concentrated under vacuum. The residue is purified by silicagel chromatography to give the title compound, m.p. 177–178° C. and $[\alpha]_D$=–72.0° (20° C., c=1).

Similar to the above described working examples the compounds of the following tables may be obtained.

Table 1

Compounds of the general structure I.1, wherein R$_2$–R$_6$, R$_{2A}$, X, Y, m, p and q correspond with a line of table A.

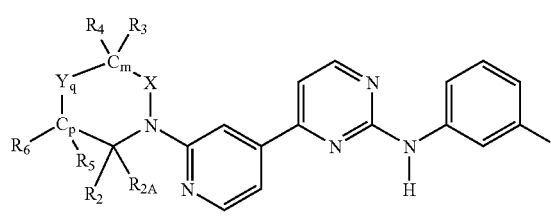

Table 2

Compounds of the general structure I.2, wherein R$_2$–R$_6$, R$_{2A}$, X, Y, m, p and q correspond with a line of table A.

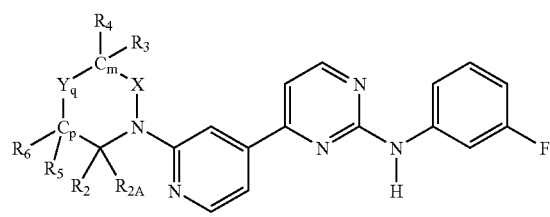

Table 3

Compounds of the general structure I.3, wherein R$_2$–R$_6$, R$_{2A}$, X, Y, m, p and q correspond with a line of table A.

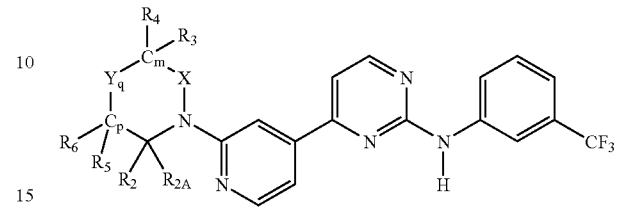

Table 4

Compounds of the general structure I.4, wherein R$_2$–R$_6$, R$_{2A}$, X, Y, m, p and q correspond with a line of table A.

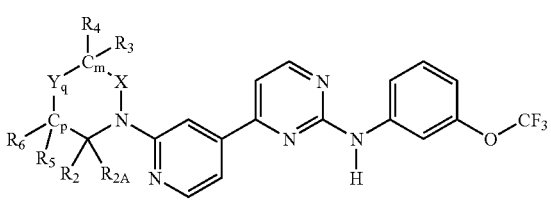

Table 5

Compounds of the general structure I.5, wherein R$_2$–R$_6$, R$_{2A}$, X, Y, m, p and q correspond with a line of table A.

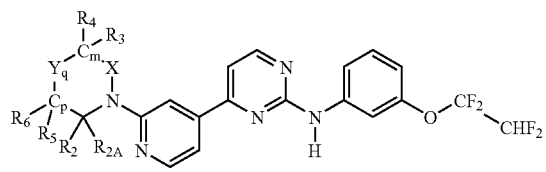

Table 6

Compounds of the general structure I.5, wherein R$_2$–R$_6$, R$_{2A}$, X, Y, m, p and q correspond with a line of table A.

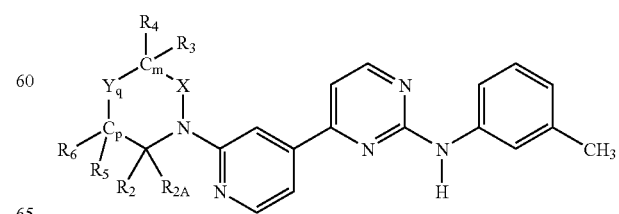

Table 7

Compounds of the general structure I.7, wherein $R_2$–$R_6$, $R_{2A}$, X, Y, m, p and q correspond with a line of table A.

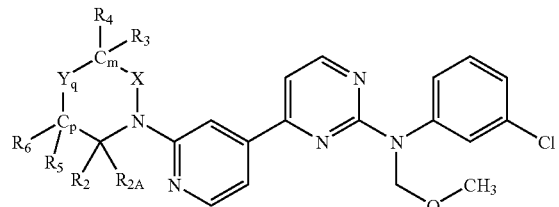

I.7

Table 8

Compounds of the general structure I.8, wherein $R_2$–$R_6$, $R_{2A}$, X, Y, m, p and q correspond with a line of table A.

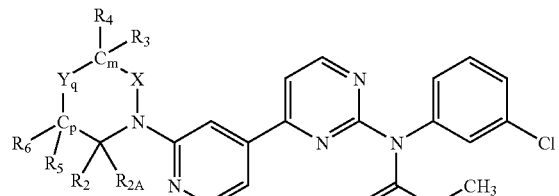

I.8

Table 9

Compounds of the general structure I.9, wherein $R_2$–$R_6$, $R_{2A}$, X, Y, m, p and q correspond with a line of table A.

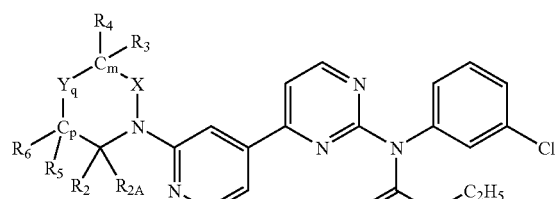

I.9

Table 10

Compounds of the general structure I.10, wherein $R_2$–$R_6$, $R_{2A}$, X, Y, m, p and q correspond with a line of table A.

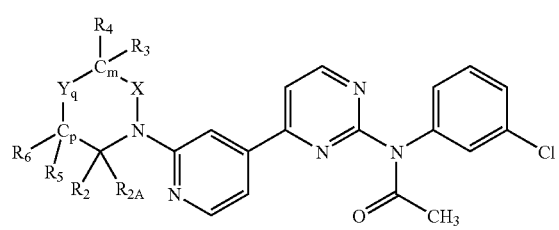

I.10

Table 11

Compounds of the general structure I.11, wherein $R_2$–$R_6$, $R_{2A}$, X, Y, m, p and q correspond with a line of table A.

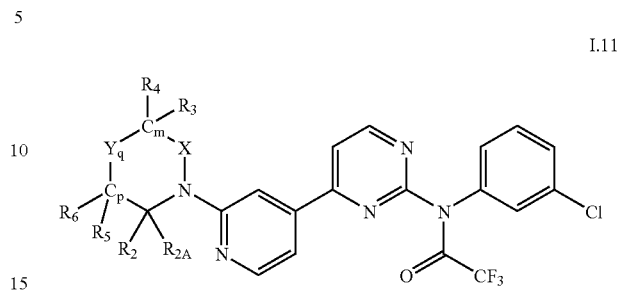

I.11

Table 12

Compounds of the general structure I.12, wherein $R_2$–$R_6$, $R_{2A}$, X, Y, m, p and q correspond with a line of table A.

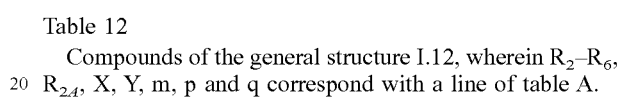

I.12

Table 13

Compounds of the general structure I.13, wherein $R_2$–$R_6$, $R_{2A}$, X, Y, m, p and q correspond with a line of table A.

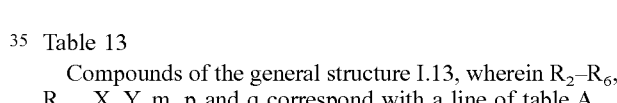

I.13

Table 14

Compounds of the general structure I.14, wherein $R_2$–$R_6$, $R_{2A}$, X, Y, m, p and q correspond with a line of table A.

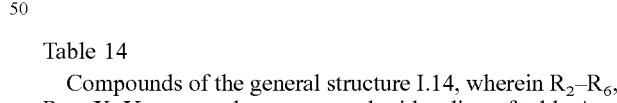

I.14

Table 15

Compounds of the general structure I.15, wherein $R_2$–$R_8$, $R_{2A}$, X, Y, m, p and q correspond with a line of table A.

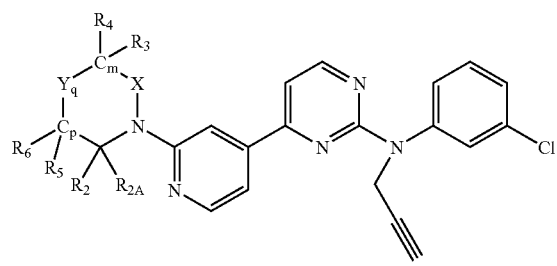

I.15

Table 16

Compounds of the general structure I.16, wherein $R_2$–$R_6$, $R_{2A}$, X, Y, m, p and q correspond with a line of table A.

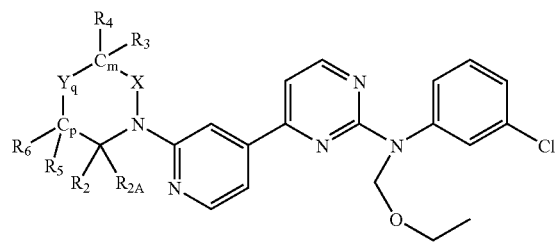

I.16

Table 17

Compounds of the general structure I.17, wherein $R_2$–$R_6$, $R_{2A}$, X, Y, m, p and q correspond with a line of table A.

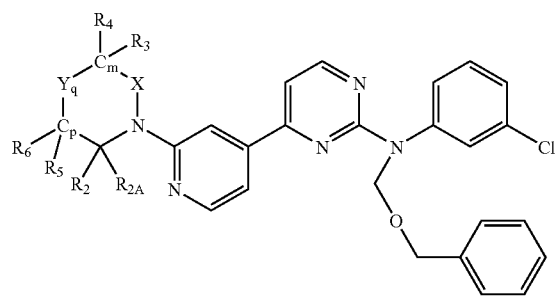

I.17

Table 18

Compounds of the general structure I.18, wherein $R_2$–$R_6$, $R_{2A}$, X, Y, m, p and q correspond with a line of table A.

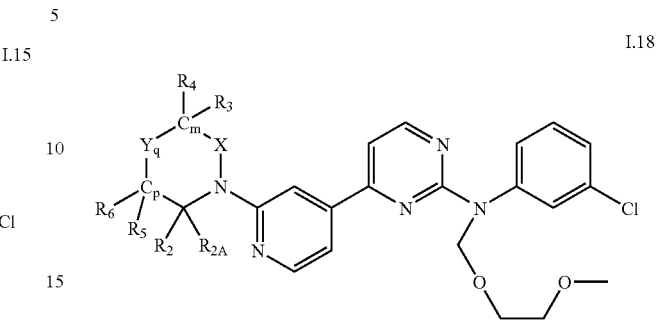

I.18

Table 19

Compounds of the general structure I.19, wherein $R_2$–$R_6$, $R_{2A}$, X, Y, m, p and q correspond with a line of table A.

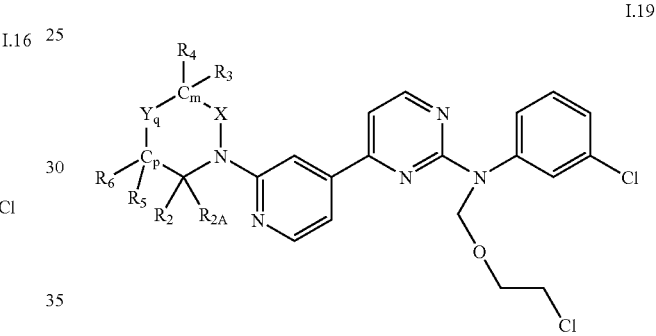

I.19

Table 20

Compounds of the general structure I.20, wherein $R_2$–$R_6$, $R_{2A}$, X, Y, m, p and q correspond with a line of table A.

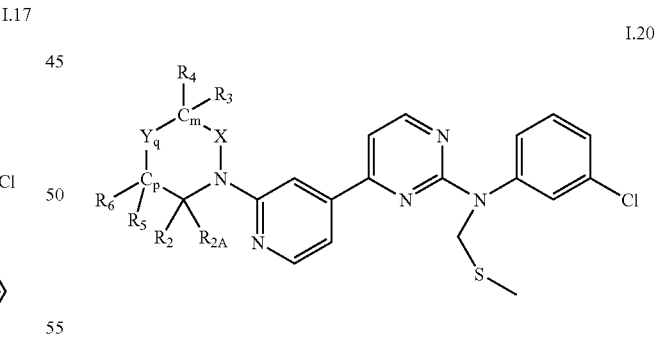

I.20

Table A:

| No. | $R_2$ | $R_{2A}$ | $R_3$ | $R_4$ | $R_5$ | $R_6$ | X | Y | m | p | q |
|---|---|---|---|---|---|---|---|---|---|---|---|
| 001 | H | H | | | H | H | C=O | O | 0 | 1 | 1 |
| 002 | CH$_3$ | H | | | H | H | C=O | O | 0 | 1 | 1 |
| 003 | CH$_2$CH$_3$ | H | | | H | H | C=O | O | 0 | 1 | 1 |
| 004 | (CH$_2$)$_2$CH$_3$ | H | | | H | H | C=O | O | 0 | 1 | 1 |
| 005 | CH(CH$_3$)$_2$ | H | | | H | H | C=O | O | 0 | 1 | 1 |

-continued

| No. | $R_2$ | $R_{2A}$ | $R_3$ | $R_4$ | $R_5$ | $R_6$ | X | Y | m | p | q |
|---|---|---|---|---|---|---|---|---|---|---|---|
| 006 | H | H | | | $CH_3$ | H | C=O | O | 0 | 1 | 1 |
| 007 | $CH_3$ | H | | | $CH_3$ | H | C=O | O | 0 | 1 | 1 |
| 008 | $CH_3$ | H | | | $CH_2OH$ | H | C=O | O | 0 | 1 | 1 |
| 009 | $CH_3$ | H | | | $(CH_2)_2OH$ | H | C=O | O | 0 | 1 | 1 |
| 010 | $CH_3$ | H | | | $CH_2OCH_3$ | H | C=O | O | 0 | 1 | 1 |
| 011 | $CH_3$ | H | | | $(CH_2)_2OCH_3$ | H | C=O | O | 0 | 1 | 1 |
| 012 | H | H | | | $CH_3$ | $CH_3$ | C=O | O | 0 | 1 | 1 |
| 013 | $CH_3$ | H | | | $CH_3$ | $CH_3$ | C=O | O | 0 | 1 | 1 |
| 014 | $CH_2CH_3$ | H | | | $CH_3$ | $CH_3$ | C=O | O | 0 | 1 | 1 |
| 015 | H | H | | | H | H | C=S | O | 0 | 1 | 1 |
| 016 | H | H | | | $CH_3$ | H | C=S | O | 0 | 1 | 1 |
| 017 | $CH_3$ | H | | | H | H | C=S | O | 0 | 1 | 1 |
| 018 | $CH_2CH_3$ | H | | | H | H | C=S | O | 0 | 1 | 1 |
| 019 | $CH_3$ | H | | | $CH_3$ | H | C=S | O | 0 | 1 | 1 |
| 020 | $CH_2CH_3$ | H | | | $CH_3$ | H | C=S | O | 0 | 1 | 1 |
| 021 | $CH_3$ | H | | | $CH_3$ | $CH_3$ | C=S | O | 0 | 1 | 1 |
| 022 | $CH_2CH_3$ | H | | | $CH_3$ | $CH_3$ | C=S | O | 0 | 1 | 1 |
| 023 | H | H | | | H | H | S=O | O | 0 | 1 | 1 |
| 024 | $CH_3$ | H | | | H | H | S=O | O | 0 | 1 | 1 |
| 025 | $CH_2CH_3$ | H | | | H | H | S=O | O | 0 | 1 | 1 |
| 026 | $CH_3$ | H | | | $CH_3$ | H | S=O | O | 0 | 1 | 1 |
| 027 | $CH_2CH_3$ | H | | | $CH_3$ | H | S=O | O | 0 | 1 | 1 |
| 028 | $CH_3$ | H | | | $CH_3$ | $CH_3$ | S=O | O | 0 | 1 | 1 |
| 029 | $CH_2CH_3$ | H | | | $CH_3$ | $CH_3$ | S=O | O | 0 | 1 | 1 |
| 030 | $CH_3$ | H | | | H | H | O=S=O | O | 0 | 1 | 1 |
| 031 | $CH_2CH_3$ | H | | | H | H | O=S=O | O | 0 | 1 | 1 |
| 032 | $CH_3$ | H | | | $CH_3$ | H | O=S=O | O | 0 | 1 | 1 |
| 033 | $CH_2CH_3$ | H | | | $CH_3$ | H | O=S=O | O | 0 | 1 | 1 |
| 034 | $CH_3$ | H | | | $CH_3$ | $CH_3$ | O=S=O | O | 0 | 1 | 1 |
| 035 | $CH_2CH_3$ | H | | | $CH_3$ | $CH_3$ | O=S=O | O | 0 | 1 | 1 |
| 036 | $CH_3$ | H | | | H | H | C=O | S | 0 | 1 | 1 |
| 037 | $CH_2CH_3$ | H | | | H | H | C=O | S | 0 | 1 | 1 |
| 038 | $CH_3$ | H | | | $CH_3$ | H | C=O | S | 0 | 1 | 1 |
| 039 | $CH_2CH_3$ | H | | | $CH_3$ | H | C=O | S | 0 | 1 | 1 |
| 040 | $CH_3$ | H | | | $CH_3$ | $CH_3$ | C=O | S | 0 | 1 | 1 |
| 041 | $CH_2CH_3$ | H | | | $CH_3$ | $CH_3$ | C=O | S | 0 | 1 | 1 |
| 042 | H | H | H | H | | | C=O | O | 1 | 0 | 1 |
| 043 | $CH_3$ | H | H | H | | | C=O | O | 1 | 0 | 1 |
| 044 | $CH_2CH_3$ | H | H | H | | | C=O | O | 1 | 0 | 1 |
| 045 | H | H | $CH_3$ | H | | | C=O | O | 1 | 0 | 1 |
| 046 | $CH_3$ | H | $CH_3$ | H | | | C=O | O | 1 | 0 | 1 |
| 047 | $CH_2CH_3$ | H | $CH_3$ | H | | | C=O | O | 1 | 0 | 1 |
| 048 | $CH_3$ | H | $CH_2OH$ | H | | | C=O | O | 1 | 0 | 1 |
| 049 | $CH_3$ | H | $(CH_2)_2OH$ | H | | | C=O | O | 1 | 0 | 1 |
| 050 | $CH_3$ | H | $CH_2OCH_3$ | H | | | C=O | O | 1 | 0 | 1 |
| 051 | $CH_3$ | H | $(CH_2)_2OCH_3$ | H | | | C=O | O | 1 | 0 | 1 |
| 052 | H | H | $CH_3$ | $CH_3$ | | | C=O | O | 1 | 0 | 1 |
| 053 | $CH_3$ | H | $CH_3$ | $CH_3$ | | | C=O | O | 1 | 0 | 1 |
| 054 | $CH_2CH_3$ | H | $CH_3$ | $CH_3$ | | | C=O | O | 1 | 0 | 1 |
| 055 | $CH_3$ | H | H | H | | | C=S | O | 1 | 0 | 1 |
| 056 | $CH_2CH_3$ | H | H | H | | | C=S | O | 1 | 0 | 1 |
| 057 | $CH_3$ | H | $CH_3$ | H | | | C=S | O | 1 | 0 | 1 |
| 058 | $CH_2CH_3$ | H | $CH_3$ | H | | | C=S | O | 1 | 0 | 1 |
| 059 | $CH_3$ | H | $CH_3$ | $CH_3$ | | | C=S | O | 1 | 0 | 1 |
| 060 | $CH_2CH_3$ | H | $CH_3$ | $CH_3$ | | | C=S | O | 1 | 0 | 1 |
| 061 | $CH_3$ | H | H | H | | | S=O | O | 1 | 0 | 1 |
| 062 | $CH_2CH_3$ | H | H | H | | | S=O | O | 1 | 0 | 1 |
| 063 | $CH_3$ | H | $CH_3$ | H | | | S=O | O | 1 | 0 | 1 |
| 064 | $CH_2CH_3$ | H | $CH_3$ | H | | | S=O | O | 1 | 0 | 1 |
| 065 | $CH_3$ | H | $CH_3$ | $CH_3$ | | | S=O | O | 1 | 0 | 1 |
| 066 | $CH_2CH_3$ | H | $CH_3$ | $CH_3$ | | | S=O | O | 1 | 0 | 1 |
| 067 | $CH_3$ | H | H | H | | | O=S=O | O | 1 | 0 | 1 |
| 068 | $CH_2CH_3$ | H | H | H | | | O=S=O | O | 1 | 0 | 1 |
| 069 | $CH_3$ | H | $CH_3$ | H | | | O=S=O | O | 1 | 0 | 1 |
| 070 | $CH_2CH_3$ | H | $CH_3$ | H | | | O=S=O | O | 1 | 0 | 1 |
| 071 | $CH_3$ | H | $CH_3$ | $CH_3$ | | | O=S=O | O | 1 | 0 | 1 |
| 072 | $CH_2CH_3$ | H | $CH_3$ | $CH_3$ | | | O=S=O | O | 1 | 0 | 1 |
| 073 | $CH_3$ | H | H | H | | | C=O | S | 1 | 0 | 1 |
| 074 | $CH_2CH_3$ | H | H | H | | | C=O | S | 1 | 0 | 1 |
| 075 | $CH_3$ | H | $CH_3$ | H | | | C=O | S | 1 | 0 | 1 |
| 076 | $CH_2CH_3$ | H | $CH_3$ | H | | | C=O | S | 1 | 0 | 1 |
| 077 | $CH_3$ | H | $CH_3$ | $CH_3$ | | | C=O | S | 1 | 0 | 1 |
| 078 | $CH_2CH_3$ | H | $CH_3$ | $CH_3$ | | | C=O | S | 1 | 0 | 1 |
| 079 | H | H | H | H | H | H | C=O | | 1 | 1 | 0 |
| 080 | $CH_3$ | H | H | H | H | H | C=O | | 1 | 1 | 0 |
| 081 | $CH_2CH_3$ | H | H | H | H | H | C=O | | 1 | 1 | 0 |
| 082 | H | H | $CH_3$ | H | H | H | C=O | | 1 | 1 | 0 |

-continued

| No. | R₂ | R₂ₐ | R₃ | R₄ | R₅ | R₆ | X | Y | m | p | q |
|---|---|---|---|---|---|---|---|---|---|---|---|
| 083 | CH₃ | H | CH₃ | H | H | H | C=O | | 1 | 1 | 0 |
| 084 | CH₂CH₃ | H | CH₃ | H | H | H | C=O | | 1 | 1 | 0 |
| 085 | CH₃ | H | CH₂OH | H | H | H | C=O | | 1 | 1 | 0 |
| 086 | CH₃ | H | (CH₂)₂OH | H | H | H | C=O | | 1 | 1 | 0 |
| 087 | CH₃ | H | CH₂OCH₃ | H | H | H | C=O | | 1 | 1 | 0 |
| 088 | CH₃ | H | (CH₂)₂OCH₃ | H | H | H | C=O | | 1 | 1 | 0 |
| 089 | H | H | CH₃ | CH₃ | H | H | C=O | | 1 | 1 | 0 |
| 090 | CH₃ | H | CH₃ | CH₃ | H | H | C=O | | 1 | 1 | 0 |
| 091 | CH₂CH₃ | H | CH₃ | CH₃ | H | H | C=O | | 1 | 1 | 0 |
| 092 | H | H | H | H | CH₃ | H | C=O | | 1 | 1 | 0 |
| 093 | CH₃ | H | H | H | CH₃ | H | C=O | | 1 | 1 | 0 |
| 094 | CH₂CH₃ | H | H | H | CH₃ | H | C=O | | 1 | 1 | 0 |
| 095 | CH₃ | H | H | H | CH₂OH | H | C=O | | 1 | 1 | 0 |
| 096 | CH₃ | H | H | H | (CH₂)₂OH | H | C=O | | 1 | 1 | 0 |
| 097 | CH₃ | H | H | H | CH₂OCH₃ | H | C=O | | 1 | 1 | 0 |
| 098 | CH₃ | H | H | H | (CH₂)₂OCH₃ | H | C=O | | 1 | 1 | 0 |
| 099 | H | H | H | H | CH₃ | CH₃ | C=O | | 1 | 1 | 0 |
| 100 | CH₃ | H | H | H | CH₃ | CH₃ | C=O | | 1 | 1 | 0 |
| 101 | CH₂CH₃ | H | H | H | CH₃ | CH₃ | C=O | | 1 | 1 | 0 |
| 102 | H | H | CH₃ | H | CH₃ | H | C=O | | 1 | 1 | 0 |
| 103 | CH₃ | H | CH₃ | H | CH₃ | H | C=O | | 1 | 1 | 0 |
| 104 | CH₂CH₃ | H | CH₃ | H | CH₃ | H | C=O | | 1 | 1 | 0 |
| 105 | CH₃ | H | CH₃ | CH₃ | CH₃ | H | C=O | | 1 | 1 | 0 |
| 106 | CH₂CH₃ | H | CH₃ | CH₃ | CH₃ | H | C=O | | 1 | 1 | 0 |
| 107 | CH₃ | H | CH₃ | H | CH₃ | H | C=O | | 1 | 1 | 0 |
| 108 | CH₂CH₃ | H | CH₃ | H | CH₃ | H | C=O | | 1 | 1 | 0 |
| 109 | CH₃ | H | CH₃ | CH₃ | CH₃ | CH₃ | C=O | | 1 | 1 | 0 |
| 110 | CH₂CH₃ | H | CH₃ | CH₃ | CH₃ | CH₃ | C=O | | 1 | 1 | 0 |
| 111 | CH₃ | H | H | H | H | H | C=S | | 1 | 1 | 0 |
| 112 | CH₂CH₃ | H | H | H | H | H | C=S | | 1 | 1 | 0 |
| 113 | CH₃ | H | CH₃ | H | H | H | C=S | | 1 | 1 | 0 |
| 114 | CH₂CH₃ | H | CH₃ | H | H | H | C=S | | 1 | 1 | 0 |
| 115 | CH₃ | H | CH₃ | CH₃ | H | H | C=S | | 1 | 1 | 0 |
| 116 | CH₂CH₃ | H | CH₃ | CH₃ | H | H | C=S | | 1 | 1 | 0 |
| 117 | CH₃ | H | H | H | CH₃ | H | C=S | | 1 | 1 | 0 |
| 118 | CH₂CH₃ | H | H | H | CH₃ | H | C=S | | 1 | 1 | 0 |
| 119 | CH₃ | H | CH₃ | H | CH₃ | H | C=S | | 1 | 1 | 0 |
| 120 | CH₂CH₃ | H | CH₃ | H | CH₃ | H | C=S | | 1 | 1 | 0 |
| 121 | CH₃ | H | CH₃ | CH₃ | CH₃ | H | C=S | | 1 | 1 | 0 |
| 122 | CH₂CH₃ | H | CH₃ | CH₃ | CH₃ | H | C=S | | 1 | 1 | 0 |
| 123 | CH₃ | H | H | H | CH₃ | CH₃ | C=S | | 1 | 1 | 0 |
| 124 | CH₂CH₃ | H | H | H | CH₃ | CH₃ | C=S | | 1 | 1 | 0 |
| 125 | CH₃ | H | CH₃ | H | CH₃ | CH₃ | C=S | | 1 | 1 | 0 |
| 126 | CH₂CH₃ | H | CH₃ | H | CH₃ | CH₃ | C=S | | 1 | 1 | 0 |
| 127 | CH₃ | H | CH₃ | CH₃ | CH₃ | CH₃ | C=S | | 1 | 1 | 0 |
| 128 | CH₂CH₃ | H | CH₃ | CH₃ | CH₃ | CH₃ | C=S | | 1 | 1 | 0 |
| 129 | CH₃ | H | H | H | H | H | S=O | | 1 | 1 | 0 |
| 130 | CH₂CH₃ | H | H | H | H | H | S=O | | 1 | 1 | 0 |
| 131 | CH₃ | H | CH₃ | H | H | H | S=O | | 1 | 1 | 0 |
| 132 | CH₂CH₃ | H | CH₃ | H | H | H | S=O | | 1 | 1 | 0 |
| 133 | CH₃ | H | CH₃ | CH₃ | H | H | S=O | | 1 | 1 | 0 |
| 134 | CH₂CH₃ | H | CH₃ | CH₃ | H | H | S=O | | 1 | 1 | 0 |
| 135 | CH₃ | H | H | H | CH₃ | H | S=O | | 1 | 1 | 0 |
| 136 | CH₂CH₃ | H | H | H | CH₃ | H | S=O | | 1 | 1 | 0 |
| 137 | CH₃ | H | CH₃ | H | CH₃ | H | S=O | | 1 | 1 | 0 |
| 138 | CH₂CH₃ | H | CH₃ | H | CH₃ | H | S=O | | 1 | 1 | 0 |
| 139 | CH₃ | H | CH₃ | CH₃ | CH₃ | H | S=O | | 1 | 1 | 0 |
| 140 | CH₂CH₃ | H | CH₃ | CH₃ | CH₃ | H | S=O | | 1 | 1 | 0 |
| 141 | CH₃ | H | H | H | CH₃ | CH₃ | S=O | | 1 | 1 | 0 |
| 142 | CH₂CH₃ | H | H | H | CH₃ | CH₃ | S=O | | 1 | 1 | 0 |
| 143 | CH₃ | H | CH₃ | H | CH₃ | CH₃ | S=O | | 1 | 1 | 0 |
| 144 | CH₂CH₃ | H | CH₃ | H | CH₃ | CH₃ | S=O | | 1 | 1 | 0 |
| 145 | CH₃ | H | CH₃ | CH₃ | CH₃ | CH₃ | S=O | | 1 | 1 | 0 |
| 146 | CH₂CH₃ | H | CH₃ | CH₃ | CH₃ | CH₃ | S=O | | 1 | 1 | 0 |
| 147 | CH₃ | H | H | H | H | H | O=S=O | | 1 | 1 | 0 |
| 148 | CH₂CH₃ | H | H | H | H | H | O=S=O | | 1 | 1 | 0 |
| 149 | CH₃ | H | CH₃ | H | H | H | O=S=O | | 1 | 1 | 0 |
| 150 | CH₂CH₃ | H | CH₃ | H | H | H | O=S=O | | 1 | 1 | 0 |
| 151 | CH₃ | H | CH₃ | CH₃ | H | H | O=S=O | | 1 | 1 | 0 |
| 152 | CH₂CH₃ | H | CH₃ | CH₃ | H | H | O=S=O | | 1 | 1 | 0 |
| 153 | CH₃ | H | H | H | CH₃ | H | O=S=O | | 1 | 1 | 0 |
| 154 | CH₂CH₃ | H | H | H | CH₃ | H | O=S=O | | 1 | 1 | 0 |
| 155 | CH₃ | H | CH₃ | H | CH₃ | H | O=S=O | | 1 | 1 | 0 |
| 156 | CH₂CH₃ | H | CH₃ | H | CH₃ | H | O=S=O | | 1 | 1 | 0 |
| 157 | CH₃ | H | CH₃ | CH₃ | CH₃ | H | O=S=O | | 1 | 1 | 0 |
| 158 | CH₂CH₃ | H | CH₃ | CH₃ | CH₃ | H | O=S=O | | 1 | 1 | 0 |
| 159 | CH₃ | H | H | H | CH₃ | CH₃ | O=S=O | | 1 | 1 | 0 |

-continued

| No. | R₂ | R₂ₐ | R₃ | R₄ | R₅ | R₆ | X | Y | m | p | q |
|---|---|---|---|---|---|---|---|---|---|---|---|
| 160 | CH₂CH₃ | H | H | H | CH₃ | CH₃ | O=S=O | | 1 | 1 | 0 |
| 161 | CH₃ | H | CH₃ | H | CH₃ | CH₃ | O=S=O | | 1 | 1 | 0 |
| 162 | CH₂CH₃ | H | CH₃ | H | CH₃ | CH₃ | O=S=O | | 1 | 1 | 0 |
| 163 | CH₃ | H | CH₃ | CH₃ | CH₃ | CH₃ | O=S=O | | 1 | 1 | 0 |
| 164 | CH₂CH₃ | H | CH₃ | CH₃ | CH₃ | CH₃ | O=S=O | | 1 | 1 | 0 |
| 165 | CH₃ | H | | C=O | H | H | C=O | | 1 | 1 | 0 |
| 166 | CH₃ | H | | C=O | CH₃ | H | C=O | | 1 | 1 | 0 |
| 167 | CH₃ | H | | C=O | CH₂OH | H | C=O | | 1 | 1 | 0 |
| 168 | CH₃ | H | | C=O | CH₂OCH₃ | H | C=O | | 1 | 1 | 0 |
| 169 | CH₃ | H | | C=O | CH₂OCH₂CH₃ | H | C=O | | 1 | 1 | 0 |
| 170 | CH₃ | H | H | H | C=O | | C=O | | 1 | 1 | 0 |
| 171 | CH₃ | H | CH₃ | H | C=O | | C=O | | 1 | 1 | 0 |
| 172 | CH₃ | H | CH₃ | CH₃ | C=O | | C=O | | 1 | 1 | 0 |
| 173 | H | H | | | H | H | C=O | NCH₃ | 0 | 1 | 1 |
| 174 | CH₃ | H | | | H | H | C=O | NCH₃ | 0 | 1 | 1 |
| 175 | CH₂CH₃ | H | | | H | H | C=O | NCH₃ | 0 | 1 | 1 |
| 176 | H | H | | | CH₃ | H | C=O | NCH₃ | 0 | 1 | 1 |
| 177 | CH₃ | H | | | CH₃ | H | C=O | NCH₃ | 0 | 1 | 1 |
| 178 | CH₃ | H | | | CH₂OH | H | C=O | NCH₃ | 0 | 1 | 1 |
| 179 | CH₃ | H | | | (CH₂)₂OH | H | C=O | NCH₃ | 0 | 1 | 1 |
| 180 | CH₃ | H | | | CH₂OCH₃ | H | C=O | NCH₃ | 0 | 1 | 1 |
| 181 | CH₃ | H | | | (CH₂)₂OCH₃ | H | C=O | NCH₃ | 0 | 1 | 1 |
| 182 | H | H | | | CH₃ | CH₃ | C=O | NCH₃ | 0 | 1 | 1 |
| 183 | CH₃ | H | | | CH₃ | CH₃ | C=O | NCH₃ | 0 | 1 | 1 |
| 184 | CH₂CH₃ | H | | | CH₃ | CH₃ | C=O | NCH₃ | 0 | 1 | 1 |
| 185 | CH₃ | H | | | H | H | C=S | NCH₃ | 0 | 1 | 1 |
| 186 | CH₂CH₃ | H | | | H | H | C=S | NCH₃ | 0 | 1 | 1 |
| 187 | CH₃ | H | | | CH₃ | H | C=S | NCH₃ | 0 | 1 | 1 |
| 188 | CH₂CH₃ | H | | | CH₃ | H | C=S | NCH₃ | 0 | 1 | 1 |
| 189 | CH₃ | H | | | CH₃ | CH₃ | C=S | NCH₃ | 0 | 1 | 1 |
| 190 | CH₂CH₃ | H | | | CH₃ | CH₃ | C=S | NCH₃ | 0 | 1 | 1 |
| 191 | CH₃ | H | | | H | H | S=O | NCH₃ | 0 | 1 | 1 |
| 192 | CH₂CH₃ | H | | | H | H | S=O | NCH₃ | 0 | 1 | 1 |
| 193 | CH₃ | H | | | CH₃ | H | S=O | NCH₃ | 0 | 1 | 1 |
| 194 | CH₂CH₃ | H | | | CH₃ | H | S=O | NCH₃ | 0 | 1 | 1 |
| 195 | CH₃ | H | | | CH₃ | CH₃ | S=O | NCH₃ | 0 | 1 | 1 |
| 196 | CH₂CH₃ | H | | | CH₃ | CH₃ | S=O | NCH₃ | 0 | 1 | 1 |
| 197 | CH₃ | H | | | H | H | O=S=O | NCH₃ | 0 | 1 | 1 |
| 198 | CH₂CH₃ | H | | | H | H | O=S=O | NCH₃ | 0 | 1 | 1 |
| 199 | CH₃ | H | | | CH₃ | H | O=S=O | NCH₃ | 0 | 1 | 1 |
| 200 | CH₂CH₃ | H | | | CH₃ | H | O=S=O | NCH₃ | 0 | 1 | 1 |
| 201 | CH₃ | H | | | CH₃ | CH₃ | O=S=O | NCH₃ | 0 | 1 | 1 |
| 202 | CH₂CH₃ | H | | | CH₃ | CH₃ | O=S=O | NCH₃ | 0 | 1 | 1 |
| 203 | H | H | | | | | C=O | ON(CH₃) | 0 | 0 | 1 |
| 204 | CH₃ | H | | | | | C=O | ON(CH₃) | 0 | 0 | 1 |
| 205 | CH₂CH₃ | H | | | | | C=O | ON(CH₃) | 0 | 0 | 1 |
| 206 | H | H | | | | | C=O | N(CH₃)O | 0 | 0 | 1 |
| 207 | CH₃ | H | | | | | C=O | N(CH₃)O | 0 | 0 | 1 |
| 208 | CH₂CH₃ | H | | | | | C=O | N(CH₃)O | 0 | 0 | 1 |
| 209 | H | H | | | H | H | C=O | O | 0 | 2 | 1 |
| 210 | CH₃ | H | | | H | H | C=O | O | 0 | 2 | 1 |
| 211 | CH₂CH₃ | H | | | H | H | C=O | O | 0 | 2 | 1 |
| 212 | (CH₂)₂CH₃ | H | | | H | H | C=O | O | 0 | 2 | 1 |
| 213 | CH(CH₃)₂ | H | | | H | H | C=O | O | 0 | 2 | 1 |
| 214 | CH₃ | H | | | H | H | S=O | O | 0 | 2 | 1 |
| 215 | CH₂CH₃ | H | | | H | H | S=O | O | 0 | 2 | 1 |
| 216 | CH₃ | H | | | H | H | O=S=O | O | 0 | 2 | 1 |
| 217 | CH₂CH₃ | H | | | H | H | O=S=O | O | 0 | 2 | 1 |
| 218 | H | H | H | H | | | C=O | O | 2 | 0 | 1 |
| 219 | CH₃ | H | H | H | | | C=O | O | 2 | 0 | 1 |
| 220 | CH₂CH₃ | H | H | H | | | C=O | O | 2 | 0 | 1 |
| 221 | H | H | H | H | H | H | C=O | O | 1 | 1 | 1 |
| 222 | CH₃ | H | H | H | H | H | C=O | O | 1 | 1 | 1 |
| 223 | CH₂CH₃ | H | H | H | H | H | C=O | O | 1 | 1 | 1 |
| 224 | H | H | CH₃ | H | H | H | C=O | O | 1 | 1 | 1 |
| 225 | CH₃ | H | CH₃ | H | H | H | C=O | O | 1 | 1 | 1 |
| 226 | CH₂CH₃ | H | CH₃ | H | H | H | C=O | O | 1 | 1 | 1 |
| 227 | H | H | CH₃ | CH₃ | H | H | C=O | O | 1 | 1 | 1 |
| 228 | CH₃ | H | CH₃ | CH₃ | H | H | C=O | O | 1 | 1 | 1 |
| 229 | CH₂CH₃ | H | CH₃ | CH₃ | H | H | C=O | O | 1 | 1 | 1 |
| 230 | H | H | H | H | CH₃ | H | C=O | O | 1 | 1 | 1 |
| 231 | CH₃ | H | H | H | CH₃ | H | C=O | O | 1 | 1 | 1 |
| 232 | CH₂CH₃ | H | H | H | CH₃ | H | C=O | O | 1 | 1 | 1 |
| 233 | H | H | H | H | CH₃ | CH₃ | C=O | O | 1 | 1 | 1 |
| 234 | CH₃ | H | H | H | CH₃ | CH₃ | C=O | O | 1 | 1 | 1 |
| 235 | CH₂CH₃ | H | H | H | CH₃ | CH₃ | C=O | O | 1 | 1 | 1 |
| 236 | H | H | CH₃ | H | CH₃ | H | C=O | O | 1 | 1 | 1 |

-continued

| No. | R₂ | R₂ₐ | R₃ | R₄ | R₅ | R₆ | X | Y | m | p | q |
|---|---|---|---|---|---|---|---|---|---|---|---|
| 237 | CH₃ | H | CH₃ | H | CH₃ | H | C=O | O | 1 | 1 | 1 |
| 238 | CH₂CH₃ | H | CH₃ | H | CH₃ | H | C=O | O | 1 | 1 | 1 |
| 239 | CH₃ | H | CH₃ | CH₃ | CH₃ | H | C=O | O | 1 | 1 | 1 |
| 240 | CH₂CH₃ | H | CH₃ | CH₃ | CH₃ | H | C=O | O | 1 | 1 | 1 |
| 241 | CH₃ | H | CH₃ | H | CH₃ | H | C=O | O | 1 | 1 | 1 |
| 242 | CH₂CH₃ | H | CH₃ | H | CH₃ | H | C=O | O | 1 | 1 | 1 |
| 243 | CH₃ | H | CH₃ | CH₃ | CH₃ | CH₃ | C=O | O | 1 | 1 | 1 |
| 244 | CH₂CH₃ | H | CH₃ | CH₃ | CH₃ | CH₃ | C=O | O | 1 | 1 | 1 |
| 245 | CH₃ | H |  | C=O | H | H | C=O | O | 1 | 1 | 1 |
| 246 | CH₃ | H |  | C=O | CH₃ | H | C=O | O | 1 | 1 | 1 |
| 247 | CH₃ | H |  | C=O | CH₃ | CH₃ | C=O | O | 1 | 1 | 1 |
| 248 | CH₂CH₃ | H |  | C=O | H | H | C=O | O | 1 | 1 | 1 |
| 249 | CH₃ | H | H | H |  | C=O | C=O | O | 1 | 1 | 1 |
| 250 | CH₃ | H | CH₃ | H |  | C=O | C=O | O | 1 | 1 | 1 |
| 251 | CH₃ | H | CH₃ | CH₃ |  | C=O | C=O | O | 1 | 1 | 1 |
| 252 | CH₃ | H |  |  | H | H | C=O | NH | 0 | 1 | 1 |
| 253 | CH₃ | CH₃ |  |  | H | H | C=O | NH | 0 | 1 | 1 |
| 254 | H | H |  |  | H | H | C=O | NH | 0 | 1 | 1 |
| 255 | CH₃ | H |  |  | H | H | C=S | NH | 0 | 1 | 1 |
| 256 | H | H |  |  | H | H | C=S | NH | 0 | 1 | 1 |
| 257 | CH₃ | H |  |  | CH₃ | H | C=O | NH | 0 | 1 | 1 |
| 258 | CH₂CH₃ | H |  |  | H | H | C=O | NH | 0 | 1 | 1 |
| 259 | CH₂CH₃ | H |  |  | H | H | C=S | NH | 0 | 1 | 1 |
| 260 | CH₃ | CH₃ |  |  | H | H | C=O | O | 0 | 1 | 1 |
| 261 | CH₃ | CH₃ | H | H | H | H | C=O | O | 1 | 1 | 1 |
| 262 | CH₃ | CH₃ |  |  | H | H | C=S | O | 0 | 1 | 1 |
| 263 | CH₃ | CH₃ |  |  | H | H | S=O | O | 0 | 1 | 1 |
| 264 | CH₃ | CH₃ |  |  | H | H | O=S=O | O | 0 | 1 | 1 |
| 265 | CH₃ | CH₃ |  |  | H | H | C=O | S | 0 | 1 | 1 |
| 266 | CH₃ | CH₂CH₃ |  |  | H | H | C=O | O | 0 | 1 | 1 |
| 267 | CH₃ | CH₂CH₃ |  |  | H | H | C=O | S | 0 | 1 | 1 |
| 268 | CH₃ | CH₂CH₃ |  |  | H | H | C=O | NCH₃ | 0 | 1 | 1 |
| 269 | CH₃ | CH₂CH₃ |  |  | H | H | C=S | O | 0 | 1 | 1 |
| 270 | CH₃ | CH₂CH₃ |  |  | H | H | O=S=O | O | 0 | 1 | 1 |
| 271 | CH₃ | CH₃ |  |  | H | H | C=O | O | 0 | 2 | 1 |
| 272 | CH₃ | CH₂CH₂CH₃ |  |  | H | H | C=O | O | 0 | 1 | 1 |
| 273 | CH₃ | CH₃ |  | C=O | H | H | C=O | O | 1 | 1 | 1 |
| 274 | CH₃ | CH₃ |  |  | CH₃ | H | C=O | O | 0 | 1 | 1 |
| 275 |  | C=O | H | H | H | H | C=O |  | 1 | 1 | 0 |
| 276 |  | C=O |  |  | CH₃ | H | C=O | O | 0 | 1 | 1 |
| 277 |  | C=O | CH₃ | H | H | H | C=O |  | 1 | 1 | 0 |
| 278 |  | C=O | CH₃ | H | CH₃ | H | C=O |  | 1 | 1 | 0 |
| 279 |  | C=O | CH₂CH₃ | H | CH₂CH₃ | H | C=O |  | 1 | 1 | 0 |
| 280 |  | C=O | H | H | CH₃ | H | C=O |  | 1 | 1 | 0 |
| 281 |  | C=O | CH₃ | H | CH₃ | H | C=O | CH₂ | 1 | 1 | 1 |
| 282 |  | C=O | H | H | CH₃ | H | C=O | CH₂ | 1 | 1 | 1 |
| 283 |  | C=O | CH₃ | H | H | H | C=O | CH₂ | 1 | 1 | 1 |
| 284 |  | C=O | H | H | H | H | C=O | CH₂ | 1 | 1 | 1 |
| 285 |  | C=O | CH₂CH₃ | H | CH₂CH₃ | H | C=O | CH₂ | 1 | 1 | 1 |
| 286 |  | C=O | CH₂CH₃ | H | H | H | C=O | CH₂ | 1 | 1 | 1 |
| 287 |  | C=O | H | H | CH₂CH₃ | H | C=O | CH₂ | 1 | 1 | 1 |
| 288 | CF₃ | H |  |  | H | H | C=O | O | 0 | 1 | 1 |
| 289 | CF₃ | H | H | H | H | H | C=O |  | 1 | 1 | 0 |
| 290 | CF₃ | H | H | H | H | H | C=O |  | 2 | 1 | 0 |
| 291 | CF₃ | H | H | H | H | H | C=O | O | 1 | 1 | 1 |
| 292 | CF₃ | H | H | H | CH₃ | H | C=O |  | 1 | 1 | 0 |
| 293 | CF₃ | H |  |  | CH₃ | H | C=O | O | 0 | 1 | 1 |
| 294 | CF₃ | H |  |  | H | H | S=O | O | 0 | 1 | 1 |
| 295 | CF₃ | H | H | H | H | H | C=O | CH₂ | 2 | 1 | 1 |
| 296 | CH₃ | H | H | H | H | H | C=O | CH₂ | 2 | 1 | 1 |
| 297 | CH₃ | H | H | H | H | H | S=O | CH₂ | 2 | 1 | 1 |
| 298 | CH₃ | H | H | H | CH₃ | H | C=S | CH₂ | 2 | 1 | 1 |
| 299 | CH₂CH₂CH₃ | H | H | H | H | H | C=O | CH₂ | 2 | 1 | 1 |
| 300 | CH₃ | CH₃ | H | H | CH₃ | H | C=O | CH₂ | 2 | 1 | 1 |
| 301 | CF₃ | H |  |  | H | H | C=O | O | 0 | 2 | 1 |

For the following example compounds physico-chemical data have been obtained and are displayed in order to illustrate the working of the present invention, including the outlined methods of synthesis. The number of given data may not be interpreted as a limitation of the invention.

TABLE B

| Comp. No. | Melting point [° C.] or $^1$H-NMR δ in ppm | Comp. No. | Melting point [° C.] or $^1$H-NMR δ in ppm |
|---|---|---|---|
| 1.001 | 162–163 | 1.301 | 215–218 |
| 1.002 | 178–179 | 1.210 | 154–155 |
| 1.003 | 154–155 | 1.079 | 165–166 |
| 1.004 | 134–135 | 3.002 | 175–176 |
| 1.005 | 167–168 | 6.002 | 89–90 |
| 1.006 | 154–155 | 7.002 | oil** |
| 1.015 | 213–214 | 1.254 | >200 |
| 1.016 | 171–172 | 1.260 | 176–177 |
| 1.017 | 156–157 | 13.002 | 133–135 |
| 1.023 | 202–203 | 12.002 | 183–184 |
| 1.024 | 125–126 | 1.080 | 162–164 |
| 1.276 | 173–174 | 1.284 | 204–207 |
| 1.275 | 209–211 | | |
| 1.002* | 177 (S-isomer; $[α]_D$ = +70.80) | | |
| 1.002* | 177–178 (R-isomer; $[α]_D$ = −72.0°) | | |
| 1.222 | $^1$H-NMR (DMSO): 9.95 (s, 1 H); 8.57 (d, 1H); 8.53 (d, 1H); 8.36 (S, 1H); 7.89 (s, 1H); 7.80 (d, 1H); 7.65 (d, 1H); 7.42 (d, 1H); 7.19 (t, 1H); 6.88 (d, 1H); 4.57 (m, 1H); 4.15 (q, 2H); 3.80 (dq, 2H); 1.03 (d, 3H). | | |
| 14.002 | $^1$H-NMR (CDCL3): 8.75 (s, 1H); 8.44 (m, 2H); 7.62 (d, 1H); 7.40–7.20 (m, 4H); 7.12 (d, 1H); 4.97 (m, 1H); 4.57 (t, 1H); 4.13 (m, 3H); 1.50 (d, 3H); 1.30 (t, 3H). | | |
| 15.002 | $^1$H-NMR (CDCL3): 8.74 (s, 1H); 8.51 (d, 1H); 8.44 (d, 1H); 7.67 (d, 1H); 7.50 (s, 1H); 7.43–7.20 (m, 4H); 4.97 (m, 1H); 4.84 (d, 2H); 4.58 (t, 1H); 4.10 (m, 1H); 2.27 (t, 1H); 1.50 (d, 3H). | | |
| 9.002 | $^1$H-NMR (CDCL$_3$): 8.78 (s, 1H); 8.70 (s, 1H); 8.45 (d, 1H); 7.62 (m, 2H); 7.40–7.20 (m, 4H); 5.00 (m, 1H); 4.58 (t, 1H); 4.32 (q, 2H); 4.12 (dd, 1H); 1.50 (d, 3H); 1.28 (t, 3H). | | |
| 10.002 | $^1$H-NMR (DMSO): 8.88 (d, 1H); 8.81 (s, 1H); 8.60 (d, 1H); 7.98 (d, 1H); 7.82 (d, 1H); 7.50–7.18 (m, 4H); 4.90 (m, 1H); 4.58 (t, 1H); 4.13 (dd, 1H); 3.32 (s, 3H); 1.40 (d, 3H). | | |
| 16.002 | $^1$H-NMR (DMSO): 8.74 (s, 1H); 8.59 (d, 1H); 8.54 (d, 1H); 7.74 (d, 1H); 7.51–7.30 (m, 5H); 5.51 (s, 2H); 4.88 (m, 1H); 4.56 (t, 1H); 4.12 (dd, 1H); 3.31 (s, 3H); 1.38 (d, 3H). | | |
| 17002 | $^1$H-NMR (DMSO): 8.76 (s, 1H); 8.61 (d, 1H); 8.54 (d, 1H); 7.72 (d, 1H); 7.53–7.20 (M, 10H); 5.62 (s, 2H); 4.89 (m, 1H); 4.70 (s, 2H); 4.57 (m, 2H); 4.13 (dd, 1H); 1.40 (d, 3H). | | |
| 18.002 | $^1$H-NMR (DMSO): 8.75 (d, 1H); 8.61 (d, 1H); 8.55 (d, 1H); 7.76 (d, 1H); 7.55–7.35 (m, 5H); 5.53 (s, 2H); 4.90 (m, 1H); 4.57 (t, 1H); 4.13 (dd, 1H); 3.74 (dd, 2H); 3.46 (dd, 2H); 3.22 (s, 3H); 1.39 (d, 3H). | | |
| 19.002 | $^1$H-NMR (DMSO): 8.75 (s, 1H); 8.61 (d, 1H); 8.54 (d, 1H); 7.76 (d, 1H); 7.54–7.33 (m, 5H); 5.57 (s, 2H); 4.89 (m, 1H); 4.57 (t, 1H); 4.16 (dd, 1H); 3.91 (t, 2H); 3.75 (t, 2H); 1.39 (d, 3H). | | |
| 20.002 | $^1$H-NMR (DMSO): 8.73 (s, 1H); 8.58 (d, 1H); 8.55 (d, 1H); 7.76 (d, 1H); 7.56–7.35 (m, 5H); 5.36 (s, 2H); 4.90 (m, 1H); 4.58 (t, 1H); 4.13 (dd, 1H); 2.12 (s, 3H); 1.40 (d, 3H). | | |

*pure enantiomer
**NMR cf. experimental part, example 5

In the following, examples of test systems in plant protection are provided which can demonstrate the efficiency of the compounds of the formula I (designated as "active ingredient" or "test compounds"):

BIOLOGICAL EXAMPLES

Example B-1

Effect against *Puccinia graminis* on wheat
(brownrust on wheat)

a) Residual Protective Activity 1 week old wheat plants cv. Arina are treated with the formulated test-compound (0.02% active substance) in a spray chamber. Two days after application wheat plants are inoculated by spraying a spore suspension ($1 \times 10^5$ ureidospores/ml) on the test plants. After an incubation period of 1 day at +20° C. and 95% relative atmospheric humidity (r. h.) plants are kept for 9 days at +20° C. and 60% r.h. in a greenhouse. The disease incidence is assessed 10 days after inoculation.

Compounds of Tables 1 to 20 show good activity in this test.

At the indicated concentration compounds 1.002, 1.002*, 1.024, 1.080 and 7.002 exhibited over 70% control of the fungal infection in this test.

b) Systemic Activity

An aqueous spray liquor prepared from the formulated test compound (0.002% active substance, based on the volume of soil) is poured into pots with 5 days old wheat seedlings. Care is taken that the spray liquor does not come into contact with the above-ground parts of the plant. 4 days later, the plants are inoculated with a spore suspension of the fungus ($1 \times 10^5$ ureidospores/ml). After an incubation period of 1 day (95 to 100% r.h. at +20° C.), the plants are placed in a greenhouse at +20° C. 10 days after infection, the disease incidence is evaluated.

Compounds of Tables 1 to 20 show good activity in this test.

Example B-2

Effect against *Phytophthora infestans* on tomatoes
(late blight on potato)

a) Residual Protective Activity 3 week old tomato plants cv. Roter Gnom are treated with the formulated test compound (0.02% active substance) in a spray chamber. Two day after application the plants are inoculated by spraying a sporangia suspension ($2 \times 10^4$ sporangia/ml) on the test plants. After an incubation period of 4 days at +18° C. and 95% r. h. in a growth chamber the disease incidence is assessed.

Compounds of Tables 1 to 20 show good activity in this test.

At the indicated concentration compounds 1.002*, 1.079 and 7.002 exhibited over 70% control of the fungal infection in this test.

b) Systemic Activity

An aqueous suspension prepared from the formulated test compound (0.002% active substance, based on the volume of soil) is poured into pots with 3 week old. Care is taken that the spray liquor does not come into contact with the above-ground parts of the plant. 4 days later, the plants are inoculated with a sporangia suspension of the fungus ($2 \times 10^4$ sporangia/ml). After an incubation period of 4 days at +18° C. and 95% r.h. in a growth chamber the disease incidence is assessed.

Compounds of Tables 1 to 20 show good activity in this test.

At the indicated concentration compounds 1.002*, 1.079 and 7.002 exhibited over 70% control of the fungal infection in this test.

Example B-3

Effect against *Phytophthora infestans*/potato (late blight on potato)

5 week old potato plants cv. Bintje are treated with the formulated test compound (0.02% active substance) in a spray chamber. Two days after application the plants are inoculated by spraying a sporangia suspension ($1.4 \times 10^5$ sporangia/ml) on the test plants. After an incubation period of 4 days at +18° C. and 95% r. h. in a growth chamber the disease incidence is assessed.

Compounds of Tables 1 to 20 show good activity in this test.

Example B-4

Effect against *Plasmopara viticola* on grapevine (grape downy mildew)

5 week old grape seedlings cv. Gutedel are treated with the formulated test compound (0.02% active substance) in a spray chamber. One day after application grape plants are inoculated by spraying a sporangia suspension ($4 \times 10^4$ sporangia/ml) on the lower leaf side of the test plants. After an incubation period of 6 days at +22° C. and 95% r.h. in a greenhouse the disease incidence is assessed.

Compounds of Tables 1 to 20 show good activity in this test.

Example B-5

Residual protective activity against *Venturia inaegualis* on apples (scab on apple)

4 week old apple seedlings cv. McIntosh are treated with the formulated test compound (0.02% active substance) in a spray chamber. One day after application apple plants are inoculated by spraying a spore suspension ($4 \times 10^5$ conidia/ml) on the test plants. After an incubation period of 4 days at +20° C. and 95% r. h. the plants are transferred to standard greenhouse conditions at 20 and 60% r.h. where they stayed for 2 days. After another 4 day incubation period at +20° C. and 95% r. h. the disease incidence is assessed.

Compounds of Tables 1 to 20 show good activity in this test.

At the indicated concentration compounds 1.002, 7.002 and 6.002 exhibited over 70% control of the fungal infection in this test.

Example B-6

Effect against *Erysiphe graminis* on barley (powdery mildew on barley)

a) Residual Protective Activity

Barley plants, cv. Regina of approximately 8 cm height were treated with the formulated test compound (0.02% active substance) in a spray chamber and duste 2 days after inoculation with conidia of the fungus. The infected plants are placed in a greenhouse at +20° C. 6 days after infection, the fungal attack was evaluated.

Compounds of Tables 1 to 20 show good activity in this test.

At the indicated concentration compounds 1.002, 1.003, 1.024, 14.002, 15.002 and 7.002 exhibited over 70% control of the fungal infection in this test.

b) Systemic Activity

An aqueous spray liquor prepared from the formulated test compound (0.002% active substance, based on the volume of soil) is poured into pots with 5 day old barley seedlings. Care is taken that the spray liquor does not come into contact with the above-ground parts of the plant. 4 days later, the plants are dusted with conidia of the fungus. The infected plants are placed in a greenhouse at +20° C. 6 days after infection, the disease incidence is evaluated.

Compounds of Tables 1 to 20 show good activity in this test.

Example B-7

*Botrytis cinerea*/grape (*botrytis* on grapes)

5 week old grape seedlings cv. Gutedel are treated with the formulated test compound (0.02% active substance) in a spray chamber. Two days after application grape plants are inoculated by spraying a spore suspension ($1.5 \times 10^5$ conidia/ml) on the test plants. After an incubation period of 3 days at +20° C. and 95% r. h. in a greenhouse the disease incidence is assessed.

Compounds of Tables 1 to 20 show good activity in this test.

At the indicated concentration compounds 1.002, 1.002*, 1.003, 1.024 and 7.002 exhibited over 70% control of the fungal infection in this test.

Example B-8

Effect against *Botrytis cinerea*/tomato (*botrytis* on tomatoes)

4 week old tomato plants cv. Roter Gnom are treated with the formulated test compound 0.02% active substance) in a spray chamber. Two days after application tomato plants are inoculated by spraying a spore suspension ($1 \times 1$ 05 conidia/ml) on the test plants. After an incubation period of 4 days at +20° C. and 95% r. h. in a greenhouse the disease incidence is assessed.

Compounds of Tables 1 to 20 show good activity in this test.

At the indicated concentration compounds 1.002, 1.002*, 1.017, 1.024 and 7.002 exhibited over 70% control of the fungal infection in this test.

Example B-9

Effect against *Pyricularia orvzae*/rice (rice blast)

3 week old rice plants cv. Sasanishiki are treated with the formulated test compound (0.02% active substance) in a spray chamber. Two days after application rice plants are inoculated by spraying a spore suspension ($1 \times 10^5$ conidia/ml) on the test plants. After an incubation period of 6 days at +25° C. and 95% r. h. the disease incidence is assessed.

Compounds of Tables 1 to 20 show good activity in this test.

At the indicated concentration compounds 1.024 and 7.002 exhibited over 70% control of the fungal infection in this test.

Example B-10

Effect against *Pyrenophora teres* (*Helminthosporium*)/barley (net blotch on barley)

1 week old barley plants cv. Regina are treated with a formulated test compound (0.02% active substance) in a spray chamber. Two days after application barley plants are inoculated by spraying a spore suspension ($3 \times 10^4$ conidia/ml) on the test plants. After an incubation period of 2 days at +20° C. and 95% r.h. the disease incidence is assessed.

Compounds of Tables 1 to 20 show good activity in this test.

At the indicated concentration compounds 1.001, 1.002, 1.002*, 1.003, 1.004, 1.017, 1.023, 1.024, 1.079, 1.275, 3.002, 6.002 and 7.002 exhibited over 70% control of the fungal infection in this test.

Example B-11

Effect against *Fusarium culmorum*/wheat (*fusarium* head blight on wheat)

A conidia suspension of *F. culmorum* ($7 \times 10^5$ conidia/ml) is mixed with the formulated test compound (0.002% active substance). The mixture is applied into a pouch which has been equipped before with a filter paper. After the application wheat seeds (cv. Orestis) are sown into the upper fault of the filter paper. The prepared pouches are then incubated for 11 days at approx. +10° C. to +18° C. and a relative humidity of 100% with a light period of 14 hours. The evaluation is made by assessing the degree of disease occurrence in the form of brown lesions on the roots.

Compounds of Tables 1 to 20 show good activity in this test.

At the indicated concentration compounds 1.002, 1.004, 1.005 and 7.002 exhibited over 70% control of the fungal infection in this test.

Example B-12

Effect Against *Septoria nodorum*/wheat (*septoria* leaf spot on wheat)

1 week old wheat plants cv. Arina are treated with a formulated test compound (0.02% active substance) in a spray chamber. One day after application wheat plants are inoculated by spraying a spore suspension ($6 \times 10^5$ conidia/ml) on the test plants. After an incubation period of 1 day at +22° C. and 95% r.h. plants are kept for 7 days at +22° C. and 60% r.h. in a greenhouse. The disease incidence is assessed 8 days after inoculation.

Compounds of Tables 1 to 20 show good activity in this test.

At the indicated concentration compounds 1.002, 1.002*, 1.003, 1.004, 1.017, 1.024, 1.079, 1.080, 1.260, 1.275, 3.002, 6.002, 10.002, 9.002, 14.002, 15.002, and 7.002 exhibited over 70% control of the fungal infection in this test.

The invention claimed is:

1. A compound of formula I

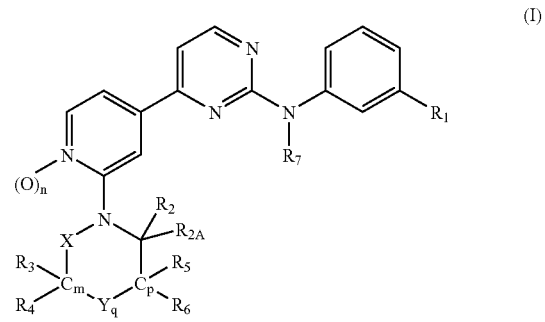

wherein
the sum of (m+p) together is 0, 1, 2 or 3;
n and q are independently of each other 0 or 1, and the sum of (m+p+q) together is 1, 2, 3 or 4;
$R_1$ is hydrogen, halogen, alkoxy, haloalkyl, haloalkoxy or alkyl;
$R_2$ is hydrogen, $C_1$–$C_6$-alkyl, $C_1$–$C_6$-haloalkyl or $C_1$–$C_6$-alkoxy;
$R_{2A}$ is hydrogen, $C_1$–$C_6$-alkyl, $C_3$–$C_4$-alkenyl or $C_3$–$C_4$-alkynyl;
each of $R_3$, $R_4$, $R_5$ and $R_6$ is, independently of the others, hydrogen, $C_1$–$C_6$-alkyl, $C_1$–$C_6$-haloalkyl, hydroxy-$C_1$–$C_6$-alkyl or $C_1$–$C_6$-alkoxy-$C_1$–$C_6$-alkyl, or the ring members $CR_3R_4$ or $CR_5R_6$ or $CR_2R_{2A}$ are independently of each other a carbonyl group (C=O) or a group C=S;
X is C=O, C=S, S=O or O=S=O;
Y is O, S, C=O, $CH_2$, —N($R_8$)—, —O—N($R_8$)—, —N($R_8$)—O— or —NH—;
$R_7$ is hydrogen, $C_1$–$C_4$-alkyl, $C_3$–$C_4$-alkenyl, $C_3$–$C_4$-alkynyl, —$CH_2OR_8$, $CH_2SR_8$, —C(O)$R_8$, —C(O)O$R_8$, $SO2R_8$, $SOR_8$ or $SR_8$; and
$R_8$ is $C_1$–$C_8$-alkyl, $C_1$–$C_8$-alkoxyalkyl, $C_1$–$C_8$ haloalkyl or phenyl$C_1$–$C_2$-alkyl wherein the phenyl may be substituted by up to three groups selected from halo or $C_1$–$C_4$-alkyl;
or a salt thereof.

2. A compound according to claim 1, wherein the moiety

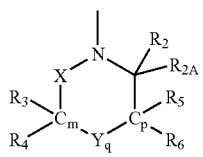

represents a ring system selected from N-oxazolidin-2-one, N-oxazolidin-2-thione, N-[1,2,3]oxathiazolidine-2-oxide, N-[1,2,3]oxathiazolidine-2,2-dioxide, N-pyrrolidin-2-one, N-pyrrolidin-2-thione, N-pyrrolidine-2,5-dione, N-thiazolidin-2-one, N-4-methylene-oxazolidin-2-one, N-piperidine-2,6-dione, N-morpholine-2,3-dione, N-morpholine-2,5-dione, N-imidazolidin-2-one, N-[1,2,4]-oxazolidin-5-one, N-[1,2,4]-oxazolidin-3-one, N-[1,2,5]oxadiazinan-6-one, N-[1,2,4]oxadiazinan-3-one, azepan-2-one or [1,3]oxazinan-2-one.

3. A compound according to claim 1, wherein $R_1$ is chlorine, fluorine, trifluoromethyl, trifluoromethoxy, or 1,1,2,2-tetrafluoroethoxy.

4. A compound according to claim 1, wherein $R_2$ is hydrogen, methyl, trifluoromethyl or ethyl and $R_{2A}$ is hydrogen or methyl.

5. A compound according to claim 1, wherein $R_7$ is hydrogen, methyl, ethyl, allyl, propargyl, methoxymethyl, thiomethoxymethyl or ethoxymethyl.

6. A compound according to claim 1, wherein X is carbonyl, C=S, or S=O and Y is oxygen and $R_3$, $R_4$, $R_5$ and $R_6$ are independently hydrogen or methyl.

7. A compound according to claim 1, wherein $R_1$ is chlorine, fluorine, trifluoromethyl, trifluoromethoxy, or 1,1,2,2-tetrafluoroethoxy; $R_2$ is hydrogen, methyl, trifluoromethyl or ethyl; $R_{2A}$ is hydrogen or methyl; $R_5$ and $R_6$ independently of each other are hydrogen, methyl, hydroxymethyl, hydroxyethyl, or methoxyethyl; $R_7$ is hydrogen, methyl, ethyl, allyl, propargyl, or methoxymethyl; X is carbonyl, C=S, or S=O; Y is oxygen, sulfur, —O—N(CH$_3$)—, or —N(CH$_3$)—O—; m and n are zero and p and q are each one.

8. A compound according to claim 1, wherein $R_1$ is chlorine; $R_2$ is methyl or trifluoromethyl; $R_{2A}$ is hydrogen or methyl; one of $R_5$ and $R_6$ is hydrogen or methyl, while the other one is hydrogen, methyl, hydroxymethyl, hydroxyethyl, or methoxyethyl; $R_7$ is hydrogen or methoxymethyl; X is carbonyl; Y is oxygen; m and n are zero and p and q are each one.

9. A compound according to claim 1, wherein $R_1$ is chlorine; $R_2$ is methyl; $R_{2A}$ is hydrogen; $R_5$ and $R_6$ independently of each other are hydrogen or methyl; $R_7$ is hydrogen or methoxymethyl; X is carbonyl; Y is oxygen; m and n are zero and p and q are each one.

10. A compound according to claim 1, selected from the group comprising of

3-{4-[2-(3-chloro-phenylamino)-pyrimidin-4-yl]-pyridin-2-yl}-oxazolidin-2-one,

N-{4-[2-(3-chloro-phenylamino)-pyrimidin-4-yl]-pyridin-2-yl}-pyrrolidin-2-one, (3-chloro-phenyl)-{4-[2-(2-oxo-[1,2,3]oxathiazolidin-3-yl)-pyridin-4-yl]-pyrimidin-2-yl}-amine, 3-{4-[2-(3-fluoro-phenylamino)-pyrimidin-4-yl]-pyridin-2-yl}-4-methyl-oxazolidin-2-one, 3-{4-[2-(3-trifluoromethyl-phenylamino)-pyrimidin-4-yl]-pyridin-2-yl}-4-methyl-oxazolidin-2-one, (3-chloro-phenyl)-{4-[2-(4-methyl-2-oxo-[1,2,3]oxathiazolidin-3-yl)-pyridin-4-yl]-pyrimidin-2-yl}-amine, 1-{4-[2-(3-chloro-phenylamino)-pyrimidin-4-yl]-pyridin-2-yl}-5-methyl-pyrrolidin-2-one, 3-{4-[2-(3-chloro-phenylamino)-pyrimidin-4-yl]-pyridin-2-yl}-4-ethyl-oxazolidin-2-one, 3-{4-[2-(3-chloro-phenylamino)-pyrimidin-4-yl]-pyridin-2-yl}-4-n-propyl-oxazolidin-2-one, 3-{4-[2-(3-chloro-phenylamino)-pyrimidin-4-yl]-pyridin-2-yl}-4-i-propyl-oxazolidin-2-one, 3-{4-[2-(3-chloro-phenylamino)-pyrimidin-4-yl]-pyridin-2-yl}-5-methyl-oxazolidin-2-one, 3-{4-[2-(3-chloro-phenylamino)-pyrimidin-4-yl]-pyridin-2-yl}-4-methyl-oxazolidin-2-one, 3-{4-[2-(3-chloro-phenylamino)-pyrimidin-4-yl]-pyridin-2-yl}-4-methyl-oxazolidine-2-thione, (S)-3-{4-[2-(3-Chloro-phenylamino)-pyrimidin-4-yl]-pyridin-2-yl}-4-methyl-oxazolidin-2-one, 3-{4-[2-(3-Chloro-phenylamino)-pyrimidin-4-yl]-pyridin-2-yl}-4-trifluoromethyl-oxazolidin-2-one, (R)-3-{4-[2-(3-Chloro-phenylamino)-pyrimidin-4-yl]-pyridin-2-yl}-4-methyl-oxazolidin-2-one, 3-{4-[2-(3-Chloro-phenylamino)-pyrimidin-4-yl]-pyridin-2-yl}-4-trifluoromethyl-[1,3]oxazinan-2-one 3-{4-[2-(3-Chloro-phenylamino)-pyrimidin-4-yl]-pyridin-2-yl}-4-methyl-[1,3]oxazinan-2-one, 1-{4-[2-(3-chloro-phenylamino)-pyrimidin-4-yl]-pyridin-2-yl}-5-trifluoromethyl-pyrrolidin-2-one, and 3-(4-{2-[(3-chloro-phenyl)-methoxymethyl-amino]-pyrimidin-4-yl}-pyridin-2-yl)-4-methyl-oxazolidin-2-one.

11. A process for the preparation of the compound according to claim 1, comprising a) reacting a compound of the formula (II)

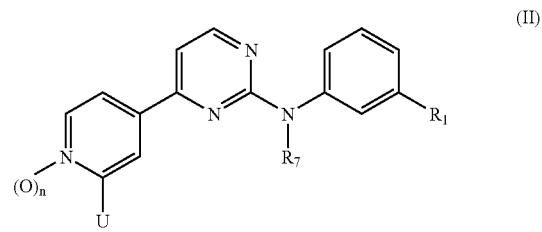

(II)

(or a salt thereof) wherein U is a leaving group, and the other moieties have the meanings given for a compound of the formula I, with a cyclic amine ring system of the formula III

(III)

(or a salt thereof) wherein $R_2$ to $R_6$, $R_{2A}$, X, Y, m, p and q have the meanings given for a compound of the formula I, in presence of a palladium catalyst or in the presence of a base, or b) cyclizing a compound of the formula IV

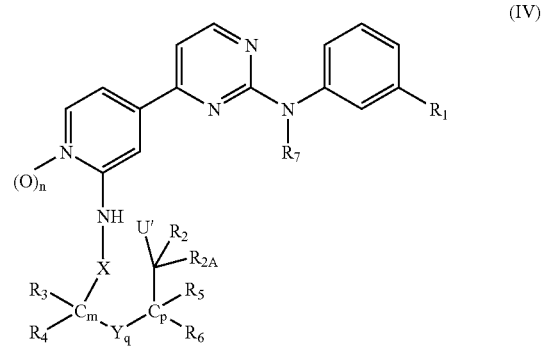

(IV)

wherein $R_1$ to $R_7$, $R_{2A}$, X, Y, n, m, p and q have the meanings given for a compound of the formula I and U' is a leaving group, by heating it optionally in presence of a base, or c) reacting a compound of the formula V

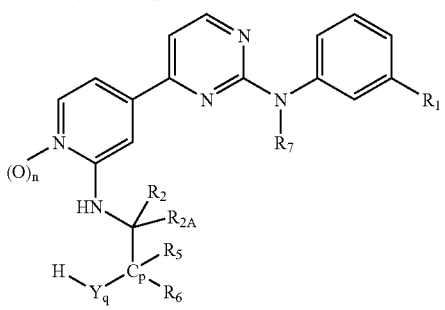

(V)

wherein q is 1 and $R_1$, $R_2$, $R_{2A}$, $R_5$, $R_6$, $R_7$, Y, n and p have the meanings given for a compound of the formula I, with phosgene, di- or triphosgene, carbonyldiimidazol, thiophosgene, thiocarbonyldiimidazol or thionylchloride thus obtaining a compound of the subformula Ia

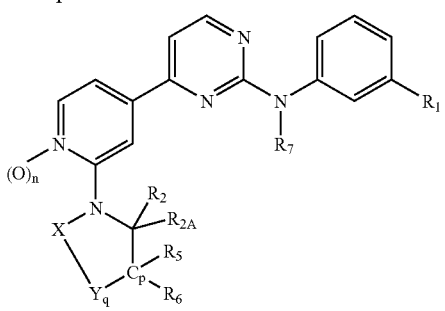

(Ia)

wherein X is C=O, C=S or S=O, q is 1 and $R_1$, $R_2$, $R_{2A}$, $R_5$, $R_6$, $R_7$, Y, n and p have the meanings given for a compound of the formula I, or d) oxidizing of a compound of the subformula Ib

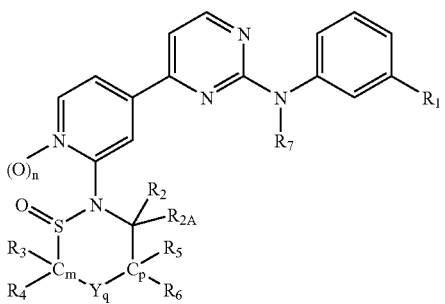

(Ib)

wherein $R_1$ to $R_7$, $R_{2A}$, Y, n, m, p and q have the meanings given for a compound of the formula I with an oxidizing amount of $NaIO_4/RuCl_3$, $NaOCl/RuO_2$ or $KMnO_4$, in order to form a compound of the formula I, wherein X is O=S=O, or e) reacting a compound of the formula VI

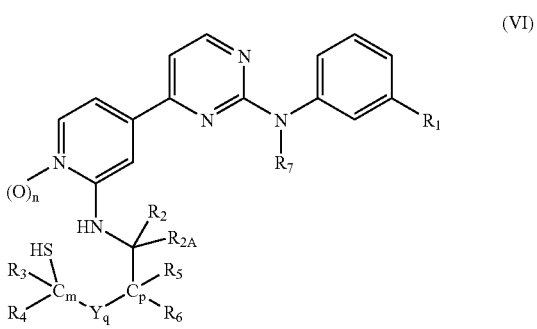

(VI)

wherein $R_1$ to $R_7$, $R_{2A}$, Y, n, m, p and q have the meanings given for a compound of the formula I with an oxidizing amount of iodine, in order to form a compound of the formula I, wherein X is S=O.

12. A composition for controlling and protecting against phytopathogenic microorganisms, comprising a compound of formula I according to claim 1 as active ingredient together with a suitable carrier.

13. A method of controlling and preventing an infestation of crop plants by phytopathogenic microorganisms, which comprises the application of a compound of formula I according to claim 1 as active ingredient to the plant, to parts of plants or to the locus thereof.

14. A method according to claim 13, wherein the phytopathogenic microorganisms are fungal organisms.

* * * * *